(12) United States Patent
Hartmann et al.

(10) Patent No.: US 9,771,314 B2
(45) Date of Patent: Sep. 26, 2017

(54) PROCESS FOR PREPARING ACRYLIC ACID FROM FORMALDEHYDE AND ACETIC ACID

(71) Applicant: BASF SE, Ludwigshafen am Rhein (DE)

(72) Inventors: Marco Hartmann, Jockgrim (DE); Lukas Schulz, Mannheim (DE); Nicolai Tonio Woerz, Darmstadt (DE); Yong Liu, Shanghai (CN); Till Christian Brueggemann, Ludwigshafen (DE); Michael Lejkowski, Neckargemuend (DE); Johannes Lieberknecht, Limburgerhof (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/348,460

(22) Filed: Nov. 10, 2016

(65) Prior Publication Data

US 2017/0129841 A1    May 11, 2017

Related U.S. Application Data

(60) Provisional application No. 62/253,699, filed on Nov. 11, 2015.

(30) Foreign Application Priority Data

Nov. 11, 2015 (DE) ......................... 10 2015 222 180

(51) Int. Cl.
*C07C 51/353* (2006.01)
*C07C 57/04* (2006.01)
(Continued)

(52) U.S. Cl.
CPC ........... *C07C 51/353* (2013.01); *B01J 27/198* (2013.01); *B01J 29/7057* (2013.01);
(Continued)

(58) Field of Classification Search
CPC combination set(s) only.
See application file for complete search history.

(56) References Cited

U.S. PATENT DOCUMENTS

2013/0085292 A1    4/2013  Mueller et al.
2016/0031789 A1*   2/2016  Schulz .................... C07C 45/38
                                                   562/598

FOREIGN PATENT DOCUMENTS

WO    WO 2016/015972 A1    2/2016

OTHER PUBLICATIONS

Ai, Mamoru, Vapor-phase aldol condensation of formaldehyde with acetic acid on V2O5—P2O5 catalysts, 1987, Journal of Catalysis, vol. 107, pp. 201-208.*

(Continued)

*Primary Examiner* — Yate K Cutliff
(74) *Attorney, Agent, or Firm* — Oblon, McClelland, Maier & Neustadt, L.L.P.

(57) ABSTRACT

The invention relates to a process for preparing acrylic acid from formaldehyde and acetic acid, comprising
(i) providing a gaseous stream S1 comprising formaldehyde, acetic acid and acrylic acid, where the molar ratio of acrylic acid to the sum total of formaldehyde and acetic acid in stream S1 is in the range from 0.005:1 to 0.3:1;
(ii) contacting stream S1 with an aldol condensation catalyst in a reaction zone to obtain a gaseous stream S2 comprising acrylic acid.

15 Claims, 4 Drawing Sheets

(51) Int. Cl.
  *C07C 51/347*  (2006.01)
  *B01J 27/198*  (2006.01)
  *B01J 29/70*   (2006.01)
  *B01J 35/00*   (2006.01)
  *B01J 35/10*   (2006.01)
  *C07C 51/43*   (2006.01)
(52) U.S. Cl.
  CPC ......... *B01J 35/002* (2013.01); *B01J 35/1019* (2013.01); *C07C 51/347* (2013.01); *C07C 51/43* (2013.01); *C07C 57/04* (2013.01)

(56) References Cited

OTHER PUBLICATIONS

James F. Vitcha, et al., "Vapor Phase Aldol Reaction", I & EC Product Research and Development, vol. 5, (1), 1966, 4 pgs.

* cited by examiner

PROCESS FOR PREPARING ACRYLIC ACID FROM FORMALDEHYDE AND ACETIC ACID

The present invention relates to a process for preparing acrylic acid from formaldehyde and acetic acid, comprising the providing of a gaseous stream S1 comprising formaldehyde, acetic acid and acrylic acid, where the molar ratio of acrylic acid to the sum total of formaldehyde and acetic acid in stream S1 is in the range from 0.005:1 to 0.3:1 and the contacting of stream S1 with an aldol condensation catalyst is effected in a reaction zone to obtain a gaseous stream S2 comprising acrylic acid.

The preparation of acrylic acid from formaldehyde and acetic acid in an aldol condensation with the aid of an aldol condensation catalyst generally gives significant amounts of unwanted byproducts, combined with an unsatisfactory selectivity in terms of acrylic acid formation and the associated yield of acrylic acid.

Vitcha and Sims, I & EC Product Research and Development, Vol. 5, No. 1, March 1966, pages 50 to 53, state that, in the synthesis of acrylic acid in a gas phase reaction proceeding from acetic acid and formaldehyde at a molar ratio of 8:1 to 10:1, high conversions and yields of acrylic acid were observed. While this excess of acetic acid leads to a higher yield of acrylic acid, this results simultaneously in an incomplete acetic acid conversion which, in order to be able to operate such a preparation process in an economically viable manner, entails an appropriate workup of the product stream and associated apparatus complexity.

Complete separation of acrylic acid from the product stream cannot sensibly be achieved in an industrial process. However, it is necessary to feed at least portions of the product stream still comprising unconverted reactants back to the process. It has been found here that acrylic acid at the reactor inlet and the reintroduction of acrylic acid into the reaction zone adversely affect both the further conversion and the selectivity of acrylic acid formation.

It was therefore an object of the present invention to provide an improved process for preparing acrylic acid from formaldehyde and acetic acid, especially with regard to selectivity in terms of acrylic acid formation and the associated yield of acrylic acid, in the case of recycling of portions of the product stream into the reaction zone.

It has been found that, surprisingly, such a process can be provided by setting the molar ratio of acrylic acid to the sum total of formaldehyde and acetic acid in stream S1 within a defined range.

The present invention therefore relates to a process for preparing acrylic acid from formaldehyde and acetic acid, comprising
(i) providing a gaseous stream S1 comprising formaldehyde, acetic acid and acrylic acid, where the molar ratio of acrylic acid to the sum total of formaldehyde and acetic acid in stream S1 is in the range from 0.005:1 to 0.3:1;
(ii) contacting stream S1 with an aldol condensation catalyst in a reaction zone to obtain a gaseous stream S2 comprising acrylic acid.

The process of the invention enables achievement of a higher selectivity in terms of acrylic acid formation and an associated increased yield of acrylic acid at a molar ratio of acrylic acid to the sum total of formaldehyde and acetic acid in stream S1 within a defined range.

Providing a Stream S1 in (i)

In step (i) of the present process, a gaseous stream S1 comprising formaldehyde, acetic acid and acrylic acid, where the molar ratio of acrylic acid to the sum total of formaldehyde and acetic acid in stream S1 is in the range from 0.005:1 to 0.3:1, is provided.

Preferably, the molar ratio of acrylic acid to the sum total of formaldehyde and acetic acid in stream S1 in (i) is in the range from 0.02:1 to 0.1:1, preferably in the range from 0.025:1 to 0.09:1, further preferably in the range from 0.03:1 to 0.08:1, further preferably in the range from 0.035:1 to 0.07:1.

In principle, stream S1 is not restricted in terms of the molar ratio of formaldehyde:acetic acid. Preferably, the molar ratio of acetic acid:formaldehyde in stream S1 in (i) is not less than 0.25:1. Likewise preferably, the molar ratio of acetic acid:formaldehyde in stream S1 in (i) is not more than 4.4:1.

Further preferably, the molar ratio of acetic acid:formaldehyde in stream S1 in (i) is in the range from 0.25:1 to 4.4:1, further preferably in the range from 0.5:1 to 2:1, further preferably in the range from 0.8:1 to 1.2:1.

Useful sources for the acetic acid in principle include any suitable source comprising at least a proportion of acetic acid. This may be acetic acid fed fresh to the process. It may likewise be acetic acid which has not been converted in the above-described process and which, for example after removal from the product stream in one or more workup steps, is recycled into the process. A combination of acetic acid fed fresh to the process and acetic acid recycled into the process is likewise possible. It is likewise possible to use acetic acid adducts, for example acetic anhydride.

Useful sources for formaldehyde likewise in principle include any suitable source comprising at least a proportion of formaldehyde. This may be formaldehyde fed fresh to the process. It may likewise be formaldehyde which has not been converted in the above-described process and which, for example after removal from the product stream in one or more workup steps, is recycled into the process. A combination of formaldehyde fed fresh to the process and formaldehyde recycled into the process is likewise possible. For example, the source used for the formaldehyde may be an aqueous formaldehyde solution (formalin). It is likewise possible to use a formaldehyde source which affords formaldehyde, for instance trioxane or paraformaldehyde.

Preferably, the source used for the formaldehyde is an aqueous formaldehyde solution. Preferably, the aqueous formaldehyde solution has a formaldehyde content in the range from 20% to 85% by weight, preferably from 30% to 80% by weight, further preferably from 40% to 60% by weight.

In principle, stream S1 is not restricted in terms of the molar ratio of acrylic acid to formaldehyde, provided that the molar ratio of acrylic acid to the sum total of formaldehyde and acetic acid is observed. Preferably, the molar ratio of acrylic acid to formaldehyde in stream S1 in (i) is in the range from 0.01:1 to 0.6:1, preferably in the range from 0.04:1 to 0.2:1, further preferably in the range from 0.05:1 to 0.18:1, further preferably in the range from 0.07:1 to 0.14:1.

It is conceivable in principle that stream S1 in (i) consists of formaldehyde, acetic acid and acrylic acid.

Preferably, stream S1 comprises at least one further component in addition to formaldehyde, acetic acid and acrylic acid, and stream S1 in (i) further preferably additionally comprises water, or inert gas, or water and inert gas.

Preferably, stream S1 in (i) additionally comprises water. In principle, stream S1 is not restricted in terms of the molar ratio of water to formaldehyde. Preferably, in stream S1 in (i), the molar ratio of water to formaldehyde is in the range from 2:1 to 0.5:1, preferably in the range from 1.7:1 to 0.6:1, further preferably in the range from 1.5:1 to 0.7:1.

It is conceivable in principle that stream S1 consists of formaldehyde, acetic acid, acrylic acid and water.

Preferably, stream S1 in (i) additionally comprises inert gas. In principle, stream S1 is not subject to any particular restrictions in terms of the inert gas content. Preferably, the inert gas content of stream S1 in (i) is in the range from 0.1% to 85.0% by volume, preferably in the range from 40% to 75% by volume, further preferably in the range from 50% to 70% by volume, based on the total volume of stream S1.

In the context of the present invention, inert gas shall be all the materials that are gaseous under the process conditions selected in each case and are inert in stage (i). "Inert" in this context means that the gaseous material in a single pass through the reaction zone is converted to an extent of less than 5 mol %, preferably to an extent of less than 2 mol %, more preferably to an extent of less than 1 mol %. Regardless of this definition, water, oxygen, carbon dioxide, carbon monoxide, propionic acid, formic acid, methanol, methyl acetate, acetaldehyde, methyl acrylate, ethene, acetone and methyl formate shall not be covered by the term "inert gas". In this context, the term "inert gas" as used in this context of present invention refers either to a single gas or to a mixture of two or more gases. For example, useful inert gases include helium, neon, argon, krypton, radon, xenon, nitrogen, sulfur hexafluoride and gas mixtures of two or more thereof.

Preferably, the inert gas in stream S1 in (i) comprises nitrogen, there being no restrictions in principle with regard to the proportion of nitrogen. Preferably, at least 95% by weight, further preferably at least 98% by weight, further preferably at least 99% by weight, of the inert gas in stream S1 in (i) consists of nitrogen.

It is conceivable in principle that stream S1 in (i) consists of formaldehyde, acetic acid, acrylic acid and inert gas. It is further conceivable that stream S1 in (i) consists of formaldehyde, acetic acid, acrylic acid, water and inert gas.

Preferably, at least 65% by volume and preferably at least 80% by volume of stream S1 in (i) consists of formaldehyde, acetic acid, acrylic acid, water and inert gas.

Preferably, stream S1 in (i) additionally comprises one or more of the compounds oxygen, carbon dioxide, carbon monoxide, propionic acid, formic acid, methanol, methyl acetate, acetaldehyde, methyl acrylate, ethene, acetone and methyl formate.

Aldol Condensation Catalyst

The term "aldol condensation catalyst" in the present context is understood to mean any catalyst capable of catalyzing an aldol condensation of the two compounds formaldehyde and acetic acid to give acrylic acid.

In principle, all suitable aldol condensation catalysts are useful in accordance with the invention. Examples, used as unsupported catalysts or in supported form, are alkali metal or alkaline earth metal oxides, mixed oxides comprising vanadium oxide, aluminosilicates or zeolites. Preferably, the aldol condensation catalyst comprises vanadium and optionally phosphorus and optionally oxygen, and also optionally tungsten.

In a preferred configuration, the aldol condensation catalyst comprises vanadium, phosphorus and oxygen, further preferably a vanadium phosphorus oxide.

Moreover, the aldol condensation catalyst in (ii) comprises a vanadium phosphorus oxide $V_xP_yO_z$ where the x:y weight ratio is preferably in the range from 1:0.5 to 1:5, further preferably from 1:0.7 to 1:4, more preferably from 1:0.8 to 1:3, and the x:z weight ratio is preferably in the range from 1:0.1 to 1:10, further preferably in the range from 1:0.5 to 1:9, more preferably in the range from 1:0.8 to 1:8.

In a further preferred configuration, the aldol condensation catalyst comprises vanadium, phosphorus and oxygen, and additionally tungsten. Further preferably, in this configuration, the aldol condensation catalyst comprises an oxidic composition comprising vanadium, tungsten, phosphorus, oxygen and optionally tin, where the molar ratio of phosphorus to the sum total of vanadium, tungsten and any tin in the oxidic composition is in the range from 1.4:1 to 2.4:1.

The aldol condensation catalyst can be used in the form of an unsupported catalyst or in supported form on one or more substances preferably selected from the group consisting of $SiO_2$, $TiO_2$, $Al_2O_3$ and $ZrO_2$ and mixtures of two or more thereof, further preferably in the form of a supported catalyst.

The aldol condensation catalyst may be present, for example, as granules or extrudates in the form of cylinders, spheres, hollow cylinders, in star form, in tablet form or as a mixture thereof. Preferably, the aldol condensation catalyst is in the form of extrudates, the cross section of the extrudates having a rectangular, triangular, hexagonal, square, polygonal, oval or circular shape. Particular preference is given to using an aldol condensation catalyst in extrudates with a round cross section, the diameter of the round cross-sectional area being in the range from 0.1 to 100 mm, preferably in the range from 0.2 to 80 mm, further preferably in the range from 0.5 to 50 mm, further preferably in the range from 1 to 30 mm, and the length of the extrudates being in the range from 0.1 to 100 mm, preferably in the range from 0.5 to 80 mm, further preferably in the range from 1 to 70 mm.

Contacting of Stream S1 with an Aldol Condensation Catalyst in (ii)

The contacting of stream S1 with an aldol condensation catalyst in (ii) in a reaction zone to obtain a gaseous stream S2 comprising acrylic acid is preferably effected continuously.

The contacting in (ii) is preferably effected in at least one reactor, preferably in at least two reactors, further preferably in at least two reactors connected in parallel, which are preferably operated in alternation, the reactors preferably being fixed bed reactors. In the alternating mode of operation, at least one reactor is always in operation. The fixed bed reactors are configured, for example, as shell and tube reactors or thermoplate reactors. In the case of a shell and tube reactor, the catalytically active fixed bed is advantageously within the catalyst tubes, with fluid heat carrier flowing around them.

The catalyst hourly space velocity with regard to the contacting in (ii) in the reactor is preferably chosen such that a balanced ratio of the parameters of conversion, selectivity, space-time yield, reactor geometry and reactor dimensions can be achieved.

Preferably, the contacting in (ii) in a fixed bed reactor is effected at a catalyst hourly space velocity in the range from 0.01 to 50 kg/(h*kg), preferably in the range from 0.1 to 40 kg/(h*kg), further preferably in the range from 0.5 to 30 kg/(h*kg), the catalyst hourly space velocity being defined as the mass of stream S1 in kg per hour and per unit mass of aldol condensation catalyst in kg.

The contacting in (ii) in the reactor is not subject to any particular restrictions with regard to the temperature of the catalyst bed, provided that the contacting of stream S1 with the aldol condensation catalyst gives a stream S2 comprising acrylic acid. Preferably, the contacting in (ii) in a fixed bed reactor is effected at a temperature of the catalyst bed in the range from 200 to 450° C., preferably in the range from 250 to 400° C., further preferably in the range from 300 to 400° C.

The contacting in (ii) in the reactor is not subject to any particular restrictions with regard to the pressure, provided that the contacting of stream S1 with the aldol condensation catalyst gives a stream S2 comprising acrylic acid. Preferably, the contacting in (ii) is effected at an absolute pressure in the range from 0.5 to 5 bar, further preferably in the range from 0.8 to 3 bar, further preferably in the range from 1 to 1.8 bar.

Stream S1 may in principle be fed to the reaction zone at any temperature suitable for the process of the invention. Preferably, stream S1 is fed to the reaction zone at a temperature at which it is entirely in gaseous form. Further preferably, stream S1 is fed to the reaction zone at a temperature in the range from 150 to 450° C., further preferably from 200 to 400° C., further preferably from 250 to 390° C.

Preferably, the stream S2 obtained in (ii) is at a temperature in the range from 200 to 450° C., preferably in the range from 250 to 400° C., further preferably in the range from 300 to 400° C.

Separation of Stream S2

Preferably, the process according to the present invention additionally comprises
- (iii) partly condensing stream S2 obtained in (ii) by cooling it down to a temperature, preferably in the range from 0 to 200° C., further preferably in the range from 20 to 150° C., further preferably in the range from 30 to 80° C., with separation of stream S2 into a condensed stream S2a and an uncondensed stream S2b, with optional intermediate storage of stream S2a in a buffer vessel.

Preferably, stream S2 additionally comprises inert gas, and stream S2a is depleted in terms of inert gas with respect to stream S2b.

The expression "depleted in terms of inert gas" as used in the context of the present invention for stream S2a with respect to stream S2b means that the proportion by weight of inert gas, based on the total weight of stream S2a, is less than the proportion by weight of inert gas based on the total weight of stream S2b.

Preferably, stream S2b is at least partly recycled into the reaction zone in (ii).

With regard to stream S2b, preferably at least 80% by volume, preferably at least 90% by volume, consists of inert gas, carbon dioxide and carbon monoxide.

The acrylic acid content of stream S2b is preferably in the range from 0.01% to 0.5% by volume, further preferably in the range from 0.02% to 0.2% by volume, further preferably in the range from 0.05% to 0.15% by volume, based on the total volume of stream S2b.

Preferably, stream S2b comprises not more than 5%, preferably from 1% to 5%, of the acrylic acid present in stream S2.

Preferably, in the process of the present invention, a portion of stream S2b is discharged from the process as purge stream. This purge stream preferably comprises not more than 30%, further preferably not more than 20%, of the total amount of stream S2b.

Preferably, stream S2a has an acrylic acid content of at least 15% by weight, preferably in the range from 20% to 60% by weight, further preferably in the range from 25% to 50% by weight, based on the total weight of stream S2a.

Stream S2a preferably comprises acrylic acid and formaldehyde, further preferably acrylic acid, formaldehyde and water, further preferably acrylic acid, formaldehyde, water and acetic acid.

Preferably, at least 90% by weight, preferably from 90% to 99% by weight, further preferably from 95% to 99% by weight, of stream S2a consists of acrylic acid, formaldehyde, water and acetic acid.

The weight ratio of acrylic acid:water in stream S2a is preferably in the range from 0.5:1 to 2.0:1, further preferably in the range from 0.8:1 to 1.8:1, further preferably in the range from 1.0:1 to 1.5:1.

Preferably, in stream S2a, the weight ratio of acrylic acid to acetic acid is in the range from 1.0:1 to 2.5:1, preferably in the range from 1.5:1 to 2.3:1, further preferably in the range from 1.7:1 to 2.1:1.

The weight ratio of acrylic acid to formaldehyde in stream 2a is preferably in the range from 2:1 to 8:1, further preferably in the range from 3:1 to 7:1, further preferably in the range from 3.5:1 to 5:1.

Preferably, stream S2a additionally comprises one or more of the compounds acetaldehyde, methanol, methyl acrylate, methyl acetate, ethene, acetone, nitrogen, carbon dioxide and carbon monoxide. Preferably, the total content of these compounds in stream S2a is preferably not more than 10% by weight, further preferably from 0.1% to 8% by weight, further preferably from 0.5% to 5% by weight.

Workup of Stream S2a

Preferably, the process according to the present invention additionally comprises
- (iv) working up stream S2a to obtain a product stream SP comprising acrylic acid and a recycling stream SR comprising acrylic acid, where the recycling stream SR comprises not more than 10% of the acrylic acid present in stream S2.

Preferably, the recycling stream SR comprises 1% to 10%, preferably from 1% to 5%, of the acrylic acid present in stream S2.

In a preferred configuration of the process of the present invention, at least a portion of the recycling stream SR is recycled into the reaction zone in (ii).

In principle, it is thus conceivable that either the recycling stream SR or stream S2b, or both streams (SR+S2b), are fed to the reaction zone in (ii). Preferably, both streams SR and S2b are fed to the reaction zone in (ii).

Preferably, stream S1 consists of a stream comprising formaldehyde and acetic acid, of the recycling stream SR and preferably additionally of stream S2b.

Preferably, the workup in (iv) in the process of the present invention comprises
- (iv.1) removing a portion of the acrylic acid present in stream S2a from stream S2a to obtain a stream S3 depleted of acrylic acid relative to stream S2a, preferably comprising formaldehyde and water, and a stream S4 enriched in acrylic acid relative to stream S2a, comprising acrylic acid and acetic acid;
- (iv.2) removing a portion of the acrylic acid present in stream S4 from stream S4 to obtain a stream S5 depleted of acrylic acid relative to stream S4, comprising acrylic acid and acetic acid, and a stream S6 enriched in acrylic acid relative to stream S4, comprising acrylic acid.

The expression "depleted of acrylic acid" as used in the context of the present invention with regard to stream S3 and stream S2 a means that the proportion by weight of acrylic acid, based on the total weight of stream S3, is less than the proportion by weight of acrylic acid based on the total weight of stream S2a. The expression "enriched in acrylic acid" as used in this context of the present invention with regard to stream S4 and stream S2a means that the proportion by weight of acrylic acid, based on the total weight of stream S4, is greater than the proportion by weight of acrylic acid in stream S2a.

Equally, the expression "depleted of acrylic acid" as used in the context of the present invention with regard to stream S5 and stream S4 means that the proportion by weight of acrylic acid, based on the total weight of stream S5, is less than the proportion by weight of acrylic acid based on the total weight of stream S4. The expression "enriched in acrylic acid" as used in this context of the present invention with regard to stream S6 and stream S4 means that the proportion by weight of acrylic acid, based on the total weight of stream S6, is greater than the proportion by weight of acrylic acid in stream S4.

The removing in (iv.1) in the process of the present invention is preferably effected by rectification. For rectificative separation, it is possible in principle to use any suitable apparatus or any suitable combination of apparatuses. Preference is given to using at least one column, further preferably one or two columns, further preferably one column, preferably equipped with separating internals.

In principle, the at least one column for the removing in (iv.1) is not restricted in terms of theoretical plates, provided that the described removing in (iv.1) is achieved. Preferably, the column has 5 to 50, preferably 10 to 40 and further preferably 15 to 30 theoretical plates.

In principle, the removing in (iv.1) can be effected at any suitable pressure, provided that the described removing in (iv.1) is achieved. Preferably, the removing in (iv.1) is effected at a pressure at the top of the column in the range from 0.1 to 2.0 bar, preferably in the range from 0.2 to 1.8 bar, further preferably in the range from 0.3 to 1.5 bar.

In principle, the removing in (iv.1) can be effected at any suitable temperature, provided that the described removing in (iv.1) is achieved. Preferably, the removing in (iv.1) is effected at a temperature in the bottom of the column in the range from 50 to 180° C., preferably in the range from 60 to 170° C., further preferably in the range from 80 to 150° C.

Preferably, stream S3 is withdrawn from the top of the column in (iv.1).

Stream S4 is preferably withdrawn from the bottom of the column in (iv.1).

Preferably, the acrylic acid content of stream S3 is in the range from 0.01% to 5% by weight, preferably in the range from 0.05% to 3% by weight, further preferably in the range from 0.1% to 2% by weight, based on the total weight of stream S3.

Preferably, the acrylic acid content of stream S4 is in the range from 40% to 80% by weight, preferably in the range from 45% to 75% by weight, further preferably in the range from 50% to 70% by weight, based on the total weight of stream S4.

Preferably, in stream S4, the weight ratio of acrylic acid:acetic acid is in the range from 4.0:1 to 0.5:1, preferably in the range from 3.5:1 to 0.8:1, further preferably in the range from 3.0:1 to 1.0:1.

Preferably, at least 80% by weight, preferably at least 90% by weight and further preferably at least 95% by weight of stream S4 consists of acrylic acid and acetic acid.

Preferably, stream S4 comprises one or more of the compounds formic acid, propionic acid, water, formaldehyde and methanol.

Preferably, the removing in (iv.2) is effected by rectification. For rectificative removal, it is possible in principle to use any suitable apparatus or any suitable combination of apparatuses. Preference is given to using at least one column, further preferably one or two columns, further preferably one column, preferably equipped with separating internals.

In principle, the at least one column for the removing in (iv.2) is not restricted in terms of theoretical plates, provided that the described removing in (iv.2) is achieved. Preferably, the column has 5 to 50, preferably 10 to 40 and further preferably 15 to 30 theoretical plates.

In principle, the removing in (iv.2) can be effected at any suitable pressure, provided that the described removing in (iv.2) is achieved. Preferably, the removing in (iv.2) is effected at a pressure at the top of the column in the range from 0.01 to 1.0 bar, preferably in the range from 0.02 to 0.8 bar, further preferably in the range from 0.05 to 0.5 bar.

In principle, the removing in (iv.2) can be effected at any suitable temperature, provided that the described removing in (iv.2) is achieved. Preferably, the removing in (iv.2) is effected at a temperature in the bottom of the column in the range from 50 to 180° C., preferably in the range from 60 to 170° C., further preferably in the range from 70 to 150° C.

Stream S5 is preferably withdrawn from the top of the column in (iv.2).

Preferably, the acrylic acid content of stream S5 is in the range from 0.1% to 30% by weight, preferably in the range from 0.5% to 25% by weight, further preferably in the range from 1.0% to 20% by weight, based on the total weight of stream S5.

Preferably, in stream S5, the weight ratio of acrylic acid:acetic acid is in the range from 0.001:1 to 0.20:1, preferably in the range from 0.005:1 to 0.15:1, further preferably in the range from 0.01:1 to 0.12:1.

Preferably, at least 85% by weight, preferably at least 90% by weight and further preferably at least 95% by weight of stream S5 consists of acrylic acid and acetic acid.

Preferably, stream S5 comprises one or more of the compounds formic acid, propionic acid, water, formaldehyde and methanol.

Preferably, stream S5, at least in part, preferably in full, is at least part of the recycling stream SR which is recycled into the reaction zone in (ii).

Preferably, stream S3, at least in part, is at least part of the recycling stream SR which is recycled into the reaction zone in (ii).

In principle, it is thus conceivable that either S5 or S3, or both, is/are at least part of the recycling stream SR. Preferably, both S5 and S3 form at least part of the recycling stream SR.

Stream S6

Preferably, at least 90% by weight, preferably from 95% to 99.9% by weight, further preferably from 98% to 99.5% by weight, of stream S6 consists of acrylic acid.

Preferably, stream S6 additionally comprises acetic acid, where the acetic acid content of stream S6 is not more than 10% by weight, preferably from 0.1% to 5% by weight, further preferably from 0.2% to 2% by weight.

Preferably, in the process of the present invention, stream S6 is the product stream SP.

Preferably, the removing in (iv.2) is effected by rectification. For rectificative removal, it is possible in principle to use any suitable apparatus or any suitable combination of apparatuses. Preference is given to using at least one column, further preferably one or two columns, further preferably one column, preferably equipped with separating internals. Stream S6 is preferably withdrawn as a side draw from the column or from the bottom of the column, preferably as a side draw from the column (iv.2).

Stream S3

With regard to S3, at least 80% by weight, preferably from 80% to 99% by weight, further preferably from 85% to 95% by weight, of this stream S3 consists of formaldehyde and water.

Preferably, the weight ratio of formaldehyde to water in stream S3 is in the range from 0.05:1 to 1:1, preferably in the range from 0.05:1 to 0.8:1, further preferably in the range from 0.1:1 to 0.5:1.

Preferably, stream S3 additionally comprises one or more of the compounds acrylic acid, acetic acid, acetaldehyde, methanol, methyl acrylate, methyl acetate, ethene, acetone, methyl formate, carbon dioxide and carbon monoxide. The total content of these compounds in stream S3 is preferably not more than 10% by weight, further preferably from 1% to 10% by weight, further preferably from 2% to 10% by weight.

Separation of Stream S3

Preferably, the workup in (iv) additionally comprises
(iv.3) at least partly separating stream S3 into a formaldehyde-enriched stream S8 and a formaldehyde-depleted stream S7.

The expression "depleted of formaldehyde" as used in the context of the present invention with regard to stream S7 and stream S3 means that the proportion by weight of formaldehyde, based on the total weight of stream S7, is less than the proportion by weight of formaldehyde based on the total weight of stream S3. The expression "enriched in formaldehyde" as used in this context of the present invention with regard to stream S8 and stream S3 means that the proportion by weight of formaldehyde, based on the total weight of stream S8, is greater than the proportion by weight of formaldehyde in stream S3.

Preferably, at least 70% by weight, preferably from 70% to 98% by weight, further preferably from 75% to 95% by weight, of stream S8 consists of formaldehyde and water.

Preferably, the weight ratio of formaldehyde to water in stream S8 is in the range from 0.25:1 to 2.0:1, preferably in the range from 0.5:1 to 1.5:1, further preferably in the range from 0.75:1 to 1.25:1.

Preferably, stream S8 additionally comprises acrylic acid, where the acrylic acid content of stream S8 is not more than 5% by weight, preferably from 0.1% to 5% by weight, further preferably 0.2% to 3% by weight.

Preferably, stream S8 additionally comprises at least one compound selected from the group consisting of acetic acid, acetaldehyde, methanol, methyl acrylate, methyl acetate, ethene, acetone and methyl formate. Preferably, the total content of these compounds in stream S8 is not more than 20% by weight, preferably from 2% to 20% by weight, further preferably from 3% to 18% by weight.

Preferably, at least 85% by weight, preferably from 90% to 99.9% by weight, further preferably from 95% to 99% by weight, of stream S7 consists of water and formaldehyde.

Preferably, stream S7 additionally comprises at least one of the compounds acrylic acid, acetic acid, acetaldehyde, methanol, methyl acrylate, methyl acetate, ethene, acetone and methyl formate. Preferably is the total content of these compounds in stream S7 not more than 15% by weight, preferably from 1% to 5% by weight.

Preferably, the separating in (iv.3) is effected by rectification. For rectificative removal, it is possible in principle to use any suitable apparatus or any suitable combination of apparatuses. Preference is given to using at least one column, further preferably one or two columns, further preferably one column, equipped with separating internals.

In principle, the at least one column for the removing in (iv.3) is not restricted in terms of theoretical plates, provided that the described removing in (iv.3) is achieved. Preferably, the column has 5 to 50, preferably 10 to 40 and further preferably 15 to 30 theoretical plates.

In principle, the removing in (iv.3) can be effected at any suitable pressure, provided that the removing in (iv.3) is achieved. Preferably, the separating in (iv.3) is effected at a pressure at the top of the column in the range from 0.01 to 2 bar, preferably in the range from 0.02 to 1.5 bar, further preferably in the range from 0.05 to 1.0 bar.

In principle, the removing in (iv.3) can be effected at any suitable temperature, provided that the removing in (iv.3) is achieved. Preferably, the separating in (iv.3) is effected at a temperature in the bottom of the column in the range from 30 to 180° C., preferably in the range from 40 to 150° C., further preferably in the range from 50 to 120° C.

Preferably, stream S8 is withdrawn from the bottom of the column in (iv.3).

Preferably, stream S7 is withdrawn from the top of the column in (iv.3).

Preferably, stream S8, at least in part, preferably in full, is at least part of the recycling stream SR which is recycled into the reaction zone in (ii).

In principle, it is thus conceivable that either S5 or S3 or S8, or S5 with S8 or S3 with S8, or all three (S3, S5, S8) is/are at least part of the recycling stream SR. Preferably, both S5 and S3 and S8 form at least part of the recycling stream SR.

Preferably, stream S5 and stream S8 are recycled together into the reaction zone in (ii).

As described in detail above, the present invention provides a highly integrated process for preparing acrylic acid in which numerous streams and partial streams can be recycled into the reaction zone, in which case these recycling operations drastically reduce the use of fresh reactants. At the same time, the molar ratio of acrylic acid to the sum total of formaldehyde and acetic acid is adjusted such that, in spite of the presence of acrylic acid, a high selectivity in terms of acrylic acid formation and an associated high yield of acrylic acid are achieved. This illustrates that the process of the invention provides an exceptionally finely adjusted, well-balanced overall process, beginning with the aldol condensation of formaldehyde and acetic acid and ending with the removal of the acrylic acid-comprising product stream, which takes account of all the chemical and energetic specifics of acrylic acid preparation and configures them advantageously in all aspects.

The present invention is illustrated in detail by the following embodiments and combinations of embodiments which are apparent from the corresponding dependency references and other references:

1. A process for preparing acrylic acid from formaldehyde and acetic acid, comprising
   (i) providing a gaseous stream S1 comprising formaldehyde, acetic acid and acrylic acid, where the molar ratio of acrylic acid to the sum total of formaldehyde and acetic acid in stream S1 is in the range from 0.005:1 to 0.3:1;
   (ii) contacting stream S1 with an aldol condensation catalyst in a reaction zone to obtain a gaseous stream S2 comprising acrylic acid.

2. The process according to embodiment 1, wherein the molar ratio of acrylic acid to the sum total of formaldehyde and acetic acid in stream S1 in (i) is in the range from 0.02:1 to 0.1:1, preferably in the range from 0.025:1 to 0.09:1, further preferably in the range from 0.03:1 to 0.08:1, further preferably in the range from 0.035:1 to 0.07:1.
3. The process according to embodiment 1 or 2, wherein the molar ratio of acetic acid:formaldehyde in stream S1 in (i) is not less than 0.25:1.
4. The process according to any of embodiments 1 to 3, wherein the molar ratio of acetic acid:formaldehyde in stream S1 in (i) is not more than 4.4:1.
5. The process according to any of embodiments 1 to 4, wherein the molar ratio of acetic acid:formaldehyde in stream S1 in (i) is in the range from 0.25:1 to 4.4:1, preferably in the range from 0.5:1 to 2:1, further preferably in the range from 0.8:1 to 1.2:1.
6. The process according to any of embodiments 1 to 5, wherein the molar ratio of acrylic acid to formaldehyde in stream S1 in (i) is in the range from 0.01:1 to 0.6:1, preferably in the range from 0.04:1 to 0.2:1, further preferably in the range from 0.05:1 to 0.18:1, further preferably in the range from 0.07:1 to 0.14:1.
7. The process according to any of embodiments 1 to 6, wherein stream S1 in (i) additionally comprises water.
8. The process according to embodiment 7, wherein, in stream S1 in (i), the molar ratio of water to formaldehyde is in the range from 2:1 to 0.5:1, preferably in the range from 1.7:1 to 0.6:1, further preferably in the range from 1.5:1 to 0.7:1.
9. The process according to any of embodiments 1 to 8, wherein stream S1 in (i) additionally comprises inert gas.
10. The process according to embodiment 9, wherein the inert gas content of stream S1 in (i) is in the range from 0.1% to 85.0% by volume, preferably in the range from 40% to 75% by volume, further preferably in the range from 50% to 70% by volume, based on the total volume of stream S1.
11. The process according to embodiment 9 or 10, wherein the inert gas in stream S1 in (i) comprises nitrogen, and preferably at least 95% by weight, further preferably at least 98% by weight, further preferably at least 99% by weight, of the inert gas consists of nitrogen.
12. The process according to any of embodiments 1 to 11, wherein at least 65% by volume and preferably at least 80% by volume of stream S1 in (i) consists of formaldehyde, acetic acid, acrylic acid, water and inert gas.
13. The process according to any of embodiments 1 to 12, wherein stream S1 in (i) additionally comprises one or more of the compounds oxygen, carbon dioxide, carbon monoxide, propionic acid, formic acid, methanol, methyl acetate, acetaldehyde, methyl acrylate, ethene, acetone and methyl formate.
14. The process according to any of embodiments 1 to 13, wherein the aldol condensation catalyst in (ii) comprises a vanadium phosphorus oxide $V_xP_yO_z$ where the x:y weight ratio is preferably in the range from 1:0.5 to 1:5, further preferably from 1:0.7 to 1:4, more preferably from 1:0.8 to 1:3, and the x:z weight ratio is preferably in the range from 1:0.1 to 1:10, further preferably in the range from 1:0.5 to 1:9, more preferably in the range from 1:0.8 to 1:8.
15. The process according to any of embodiments 1 to 13, wherein the aldol condensation catalyst in (ii) comprises an oxidic composition comprising vanadium, tungsten, phosphorus, oxygen and optionally tin, where the molar ratio of phosphorus to the sum total of vanadium, tungsten and any tin in the oxidic composition is in the range from 1.6:1 to 2.4:1.
16. The process according to embodiment 14 or 15, wherein the aldol condensation catalyst is used in the form of an unsupported catalyst or in supported form on one or more substances, preferably selected from the group consisting of $SiO_2$, $TiO_2$, $Al_2O_3$ and $ZrO_2$ and mixtures of two or more thereof, preferably in the form of a supported catalyst.
17. The process according to any of embodiments 1 to 16, wherein the contacting in (ii) is effected continuously.
18. The process according to any of embodiments 1 to 17, wherein the contacting in (ii) is effected in at least one reactor, preferably in at least two reactors, further preferably in at least two reactors connected in parallel, which are preferably operated in alternation, the reactors preferably being fixed bed reactors.
19. The process according to embodiment 16, wherein the contacting in (ii) in a fixed bed reactor is effected at a catalyst hourly space velocity in the range from 0.01 to 50 kg/(h*kg), preferably in the range from 0.1 to 40 kg/(h*kg), further preferably in the range from 0.5 to 30 kg/(h*kg), the catalyst hourly space velocity being defined as the mass of stream S1 in kg per hour and per unit mass of aldol condensation catalyst in kg.
20. The process according to embodiment 18 or 19, wherein the contacting in (ii) is effected in a fixed bed reactor at a temperature of the catalyst bed in the range from 200 to 450° C., preferably in the range from 250 to 400° C., further preferably in the range from 300 to 400° C., and at an absolute pressure in the range from 0.5 to 5 bar, further preferably in the range from 0.8 to 3 bar, further preferably in the range from 1 to 1.8 bar.
21. The process according to any of embodiments 1 to 20, wherein the stream S2 obtained in (ii) is at a temperature in the range from 200 to 450° C., preferably in the range from 250 to 400° C., further preferably in the range from 300 to 400° C.
22. The process according to any of embodiments 1 to 21, additionally comprising
  (iii) partly condensing stream S2 obtained in (ii) by cooling it down to a temperature, preferably in the range from 0 to 200° C., further preferably in the range from 20 to 150° C., further preferably in the range from 30 to 80° C., with separation of stream S2 into a condensed stream S2a and an uncondensed stream S2b, with optional intermediate storage of stream S2 a in a buffer vessel.
23. The process according to embodiment 22, wherein stream S2 additionally comprises inert gas, and stream S2a is depleted in terms of inert gas with respect to stream S2b.
24. The process according to embodiment 22 or 23, wherein stream S2b is at least partly recycled into the reaction zone in (ii).
25. The process according to any of embodiments 22 to 24, wherein at least 80% by volume and preferably at least 90% by volume of stream S2b consists of inert gas, carbon dioxide and carbon monoxide.
26. The process according to any of embodiments 22 to 25, wherein the acrylic acid content of stream S2b is in the range from 0.01% to 0.5% by volume, preferably in the range from 0.02% to 0.2% by volume, further preferably in the range from 0.05% to 0.15% by volume, based on the total volume of stream S2b.
27. The process according to any of embodiments 22 to 26, wherein stream S2b comprises not more than 5%, preferably from 1% to 5%, of the acrylic acid present in stream S2.

28. The process according to any of embodiments 22 to 25, wherein a portion of stream S2b is removed from the process as purge stream and this purge stream is preferably not more than 30%, further preferably not more than 20%, of the total amount of stream S2b.
29. The process according to any of embodiments 22 to 28, wherein stream S2a has an acrylic acid content of at least 15% by weight, preferably in the range from 20% to 60% by weight, further preferably in the range from 25% to 50% by weight, based on the total weight of stream S2a.
30. The process according to any of embodiments 22 to 29, wherein stream S2a comprises acrylic acid and formaldehyde, preferably acrylic acid, formaldehyde and water, further preferably acrylic acid, formaldehyde, water and acetic acid.
31. The process according to embodiment 30, wherein at least 90% by weight, preferably from 90% to 99% by weight, further preferably from 95% to 99% by weight, of stream S2a consists of acrylic acid, formaldehyde, water and acetic acid.
32. The process according to embodiment 30 or 31, wherein the weight ratio of acrylic acid:water in stream S2a is in the range from 0.5:1 to 2.0:1, preferably in the range from 0.8:1 to 1.8:1, further preferably in the range from 1.0:1 to 1.5:1.
33. The process according to either of embodiments 32 and 33, wherein the weight ratio of acrylic acid to acetic acid in stream S2a is in the range from 1.0:1 to 2.5:1, preferably in the range from 1.5:1 to 2.3:1, further preferably in the range from 1.7:1 to 2.1:1.
34. The process according to any of embodiments 30 to 33, wherein the weight ratio of acrylic acid to formaldehyde in stream S2a is in the range from 2:1 to 8:1, preferably in the range from 3:1 to 7:1, further preferably in the range from 3.5:1 to 5:1.
35. The process according to any of embodiments 30 to 34, wherein stream S2a additionally comprises one or more of the compounds acetaldehyde, methanol, methyl acrylate, methyl acetate, ethene, acetone, nitrogen, carbon dioxide and carbon monoxide, where the total content of these compounds in stream S2a is preferably not more than 10% by weight, further preferably from 0.1% to 8% by weight, further preferably from 0.5% to 5% by weight.
36. The process according to any of embodiments 22 to 35, preferably according to any of embodiments 22 to 35, additionally comprising
   (iv) working up stream S2a to obtain a product stream SP comprising acrylic acid and a recycling stream SR comprising acrylic acid, where the recycling stream SR comprises not more than 10% of the acrylic acid present in stream S2.
37. The process according to embodiment 36, wherein the recycling stream SR comprises 1% to 10%, preferably from 1% to 5%, of the acrylic acid present in stream S2.
38. The process according to embodiment 36 or 37, wherein at least a portion of the recycling stream SR is recycled into the reaction zone in (ii).
39. The process according to embodiment 38, wherein stream S1 consists of a stream comprising formaldehyde and acetic acid, of the recycling stream SR and preferably additionally of stream S2b.
40. The process according to either of embodiments 36 and 37, wherein the workup in (iv) comprises
   (iv.1) removing a portion of the acrylic acid present in stream S2a from stream S2a to obtain a stream S3 depleted of acrylic acid relative to stream S2a, preferably comprising formaldehyde and water, and a stream S4 enriched in acrylic acid relative to stream S2a, comprising acrylic acid and acetic acid;
   (iv.2) removing a portion of the acrylic acid present in stream S4 from stream S4 to obtain a stream S5 depleted of acrylic acid relative to stream S4, comprising acrylic acid and acetic acid, and a stream S6 enriched in acrylic acid relative to stream S4, comprising acrylic acid.
41. The process according to embodiment 40, wherein the removing in (iv.1) is effected by rectification, preferably using at least one column, further preferably one or two columns, further preferably one column, preferably equipped with separating internals.
42. The process according to embodiment 41, wherein the column has 5 to 50, preferably 10 to 40, further preferably 15 to 30, theoretical plates.
43. The process according to embodiment 41 or 42, wherein the removing in (iv.1) is effected at a pressure at the top of the column in the range from 0.1 to 2.0 bar, preferably in the range from 0.2 to 1.8 bar, further preferably in the range from 0.3 to 1.5 bar.
44. The process according to any of embodiments 41 to 43, wherein the removing in (iv.1) is effected at a temperature in the bottom of the column in the range from 50 to 180° C., preferably in the range from 60 to 170° C., further preferably in the range from 80 to 150° C.
45. The process according to any of embodiments 41 to 44, wherein stream S3 is withdrawn from the top of the column in (iv.1).
46. The process according to either of embodiments 44 and 45, wherein stream S4 is withdrawn from the bottom of the column in (iv.1).
47. The process according to any of embodiments 40 to 46, wherein the acrylic acid content of stream S3 is in the range from 0.01% to 5% by weight, preferably in the range from 0.05% to 3% by weight, further preferably in the range from 0.1% to 2% by weight, based on the total weight of stream S3.
48. The process according to any of embodiments 40 to 47, wherein the acrylic acid content of stream S4 is in the range from 40% to 80% by weight, preferably in the range from 45% to 75% by weight, further preferably in the range from 50% to 70% by weight, based on the total weight of stream S4.
49. The process according to any of embodiments 40 to 48, wherein the weight ratio of acrylic acid:acetic acid in stream S4 is in the range from 4.0:1 to 0.5:1, preferably in the range from 3.5:1 to 0.8:1, further preferably in the range from 3.0:1 to 1.0:1.
50. The process according to any of embodiments 40 to 49, wherein at least 80% by weight, preferably at least 90% by weight, further preferably at least 95% by weight, of stream S4 consists of acrylic acid and acetic acid.
51. The process according to any of embodiments 40 to 50, wherein stream S4 comprises one or more of the compounds formic acid, propionic acid, water, formaldehyde and methanol.
52. The process according to any of embodiments 40 to 51, wherein the removing in (iv.2) is effected by rectification, preferably using at least one column, further preferably one or two columns, further preferably one column, preferably equipped with separating internals.
53. The process according to embodiment 52, wherein the column has 5 to 50, preferably 10 to 40, further preferably 15 to 30, theoretical plates.
54. The process according to embodiment 52 or 53, wherein the removing in (iv.2) is effected at a pressure at the top of the column in the range from 0.01 to 1.0 bar, preferably in the range from 0.02 to 0.8 bar, further preferably in the range from 0.05 to 0.5 bar.

55. The process according to any of embodiments 52 to 54, wherein the removing in (iv.2) is effected at a temperature in the bottom of the column in the range from 50 to 180° C., preferably in the range from 60 to 170° C., further preferably in the range from 70 to 150° C.

56. The process according to any of embodiments 52 to 55, wherein stream S5 is withdrawn from the top of the column in (iv.2).

57. The process according to any of embodiments 40 to 56, wherein the acrylic acid content of stream S5 is in the range from 0.1% to 30% by weight, preferably in the range from 0.5% to 25% by weight, further preferably in the range from 1.0% to 20% by weight, based on the total weight of stream S5.

58. The process according to any of embodiments 40 to 57, wherein the weight ratio of acrylic acid:acetic acid in stream S5 is in the range from 0.001:1 to 0.20:1, preferably in the range from 0.005:1 to 0.15:1, further preferably in the range from 0.01:1 to 0.12:1.

59. The process according to any of embodiments 40 to 58, wherein at least 85% by weight, preferably at least 90% by weight, further preferably at least 95% by weight, of stream S5 consists of acrylic acid and acetic acid.

60. The process according to any of embodiments 40 to 59, wherein stream S5 comprises one or more of the compounds formic acid, propionic acid, water, formaldehyde and methanol.

61. The process according to any of embodiments 40 to 60, wherein stream S5, at least in part, preferably in full, is at least part of the recycling stream SR which is recycled into the reaction zone in (ii).

62. The process according to any of embodiments 40 to 61, wherein stream S3, at least in part, is at least part of the recycling stream SR which is recycled into the reaction zone in (ii).

63. The process according to any of embodiments 40 to 62, wherein at least 90% by weight, preferably from 95% to 99.9% by weight, further preferably from 98% to 99.5% by weight, of stream S6 consists of acrylic acid.

64. The process according to embodiment 63, wherein stream S6 additionally comprises acetic acid, where the acetic acid content of stream S6 is not more than 10% by weight, preferably from 0.1% to 5% by weight, further preferably from 0.2% to 2% by weight.

65. The process according to any of embodiments 40 to 64, wherein stream S6 is the product stream SP.

66. The process according to any of embodiments 40 to 65, wherein the removing in (iv.2) is effected by rectification, preferably using at least one column, further preferably one or two columns, further preferably one column, preferably equipped with separating internals, and wherein stream S6 is withdrawn as side draw from the column or from the bottom of the column, preferably as side draw from the column (iv.2).

67. The process according to any of embodiments 40 to 66, wherein at least 80% by weight, preferably from 80% to 99% by weight, further preferably from 85% to 95% by weight, of stream S3 consists of formaldehyde and water.

68. The process according to embodiment 67, wherein the weight ratio of formaldehyde to water in stream S3 is in the range from 0.05:1 to 1:1, preferably in the range from 0.05:1 to 0.8:1, further preferably in the range from 0.1:1 to 0.5:1.

69. The process according to embodiment 67 or 68, wherein stream S3 additionally comprises one or more of the compounds acrylic acid, acetic acid, acetaldehyde, methanol, methyl acrylate, methyl acetate, ethene, acetone, methyl formate, carbon dioxide and carbon monoxide, where the total content of these compounds in stream S3 is preferably not more than 10% by weight, further preferably from 1% to 10% by weight, further preferably from 2% to 10% by weight.

70. The process according to any of embodiments 40 to 69, wherein the workup in (iv) additionally comprises
    (iv.3) at least partly separating stream S3 into a formaldehyde-enriched stream S8 and a formaldehyde-depleted stream S7.

71. The process according to embodiment 70, wherein at least 70% by weight, preferably from 70% to 98% by weight, further preferably from 75% to 95% by weight, of stream S8 consists of formaldehyde and water.

72. The process according to embodiment 71, wherein the weight ratio of formaldehyde to water in stream S8 is in the range from 0.25:1 to 2.0:1, preferably in the range from 0.5:1 to 1.5:1, further preferably in the range from 0.75:1 to 1.25:1.

73. The process according to any of embodiments 70 to 72, wherein stream S8 additionally comprises acrylic acid, where the acrylic acid content of stream S8 is not more than 5% by weight, preferably from 0.1% to 5% by weight, further preferably from 0.2% to 3% by weight.

74. The process according to any of embodiments 70 to 73, wherein stream S8 additionally comprises at least one compound selected from the group consisting of acetic acid, acetaldehyde, methanol, methyl acrylate, methyl acetate, ethene, acetone and methyl formate, where the total content of these compounds in stream S8 is not more than 20% by weight, preferably from 2% to 20% by weight, further preferably from 3% to 18% by weight.

75. The process according to any of embodiments 70 to 74, wherein at least 85% by weight, preferably from 90% to 99.9% by weight, further preferably from 95% to 99% by weight, of stream S7 consists of water and formaldehyde.

76. The process according to any of embodiments 70 to 75, wherein stream S7 additionally comprises at least one of the compounds acrylic acid, acetic acid, acetaldehyde, methanol, methyl acrylate, methyl acetate, ethene, acetone and methyl formate, where the total content of these compounds in stream S7 is not more than 15% by weight, preferably from 1% to 5% by weight.

77. The process according to any of embodiments 70 to 76, wherein the separating in (iv.3) is effected by rectification, preferably using at least one column, further preferably one or two columns, further preferably one column, equipped with separating internals.

78. The process according to embodiment 77, wherein the column has 5 to 50, preferably 10 to 40, further preferably 15 to 30, theoretical plates.

79. The process according to embodiment 77 or 78, wherein the separating in (iv.3) is effected at a pressure at the top of the column in the range from 0.01 to 2 bar, preferably in the range from 0.02 to 1.5 bar, further preferably in the range from 0.05 to 1.0 bar.

80. The process according to any of embodiments 77 to 79, wherein the separating in (iv.3) is effected at a temperature in the bottom of the column in the range from 30 to 180° C., preferably in the range from 40 to 150° C., further preferably in the range from 50 to 120° C.

81. The process according to any of embodiments 77 to 80, wherein stream S8 is withdrawn from the bottom of the column in (iv.3).
82. The process according to any of embodiments 77 to 81, wherein stream S7 is withdrawn from the top of the column in (iv.3).
83. The process according to any of embodiments 70 to 82, wherein stream S8, at least in part, preferably in full, is at least part of the recycling stream SR which is recycled into the reaction zone in (ii).
84. The process according to any of embodiments 70 to 83, wherein stream S5 and stream S8 are recycled together into the reaction zone in (ii).

U.S. Provisional Patent Application No. 62/253,699, filed Nov. 11, 2015, is incorporated into the present application by literature reference. With regard to the abovementioned teachings, numerous changes and deviations from the present invention are possible. It can therefore be assumed that the invention, within the scope of the appended claims, can be performed differently from the way described specifically herein.

Figure 1:
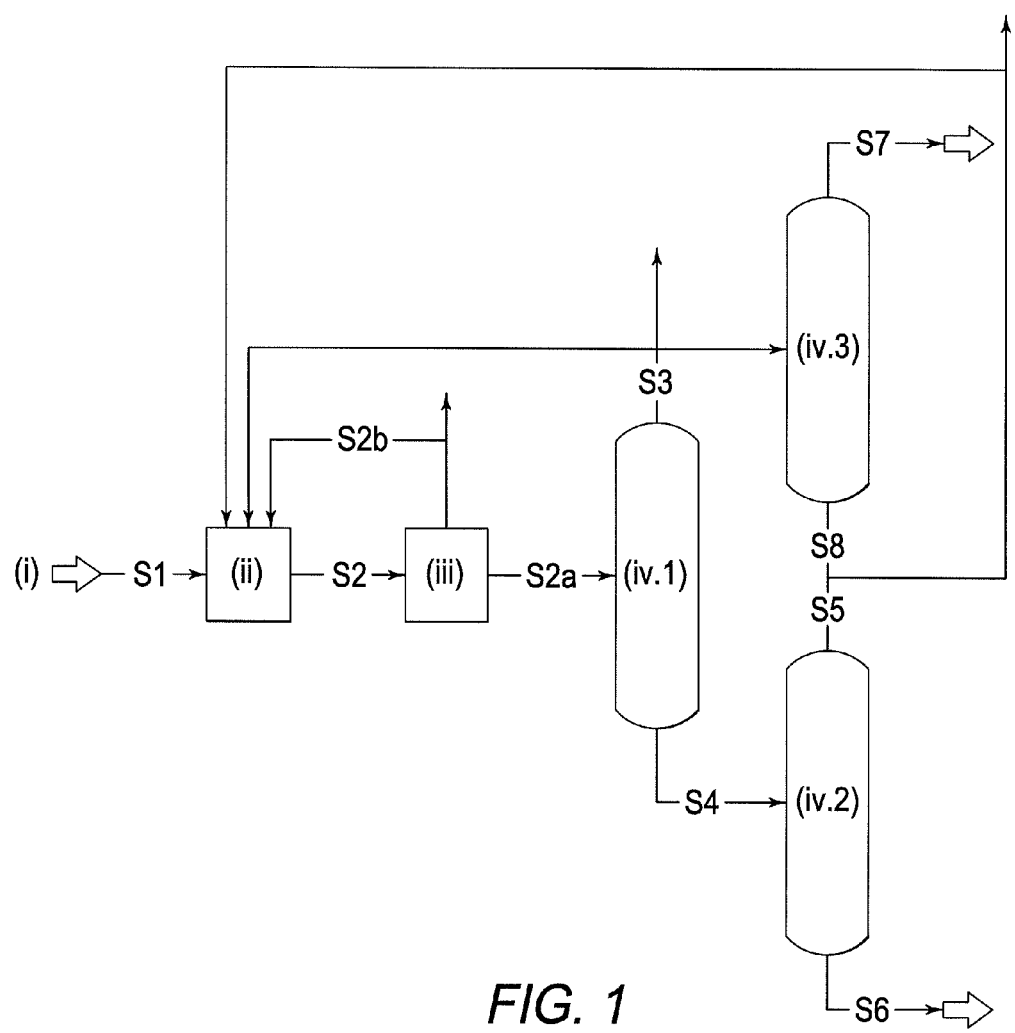
FIG. 1 shows, in schematic form, a flow diagram of the process of the invention, i.e. including the experimental set up according to example 2, with a reaction unit comprising an aldol condensation catalyst and streams S1 to S8. As well as the recycling stream SR (not shown), the recycling stream S2b (S2b_rec) is preferably present. The recycling stream SR is preferably composed of stream S3, and any further streams S5 and/or S8. In the case of simultaneous use of S5 and S8, they can, as shown, be recycled via a common conduit; an alternative option is recycling via two separate conduits (not shown).

The present invention is illustrated in detail by the examples which follow.

EXAMPLES

I. Analysis
I.1 Gas Chromatography
For gas chromatography, an instrument of the Agilent 7890 type with an FFAP column was used. The temperature program was as follows:
hold at 40° C. for 10 min;
heat to 90° C. at a heating rate of 2 K/min;
heat to 200° C. at a heating rate of 6 K/min;
heat to 250° C. at a heating rate of 25 K/min;
hold at 250° C. for 10 min.

I.2 X-Ray Diffractometry (XRD)
X-ray diffractograms (Cu K alpha radiation) were recorded on a D8 Advance series 2 diffractometer from Bruker AXS. The diffractometer was equipped with a divergence aperture opening of 0.1° and a Lynxeye detector. On the abscissa is plotted the angle (2 theta), and on the ordinate the signal intensity (Lin (counts)).
I.3 BET Measurements
The specific BET surface areas were determined by means of nitrogen adsorption at 77 K to DIN 66131.
II. Preparation of the Catalysts
II.1 Catalyst 1
Oxidic catalyst comprising vanadium and phosphorus on silica support
The catalyst was applied to a silica support by means of a two-stage incipient wetness impregnation. A vanadium oxalate solution was brought to a volume of 900 mL by adding 0.9 M oxalic acid to 1.1 mol of solid $V_2O_5$. The suspension was stirred and heated to 80° C. Solid oxalic acid dihydrate was added stepwise to the suspension until the color changed from orange to green to deep blue. The resulting solution was diluted to a total volume of one liter with 0.9 M oxalic acid. The final solution was 2.2 M with respect to vanadium (V).

41.71 mL of this vanadium oxalate solution were diluted to a volume of 42 mL with deionized water, corresponding to 100% of the liquid absorption capacity of the support. 50 g of silica (Cariact Q20-C, 1-1.6 mm gap) were impregnated with the vanadium solution. The resulting solid material was dried in a drying oven at 80° C. overnight. In a second step, 21.02 g of 85% phosphoric acid were diluted to 42 mL with deionized water and impregnated onto the solid material. The resulting solid material was dried in a drying oven at 80° C. overnight. The resulting solid material was calcined in accordance with the following temperature profile:
i) heating from room temperature to 260° C. at a rate of 1° C. per minute;
ii) heating at 260° C. for 2 hours.
II.2 Catalyst 2
Oxidic Catalyst Comprising Phosphorus and Tin on Beta-Zeolite Support
II.2.1 Preparation of a Boron-Containing Zeolitic Material Having a BEA Base Skeleton Structure
209 kg of deionized water were provided in a vessel. While stirring at 120 rpm (revolutions per minute), 355 kg of tetraethylammonium hydroxide were added and the suspension was stirred at room temperature for 10 minutes. Subsequently, 61 kg of boric acid were suspended in this water and the suspension was stirred at room temperature for a further 30 minutes. Subsequently, 555 kg of Ludox® AS-40 were added and the resulting mixture was stirred at 70 rpm at room temperature for a further hour. The liquid gel had a pH of 11.8, as measured with a pH electrode. The final mixture obtained was transferred into a crystallization vessel and heated to 160° C., at a pressure of 7.2 bar, while stirring (140 rpm) within 6 h. Subsequently, 61 kg of boric acid were suspended in water and the suspension was stirred at room temperature for a further 30 minutes. Subsequently, 61 kg of boric acid were suspended in water and the suspension was stirred at room temperature for a further 30 minutes. Then the mixture was cooled to room temperature. The mixture was heated again to 160° C. within 6 h and stirred at 140 rpm for a further 55 h. The mixture was cooled down to room temperature and then heated to a temperature of 160° C. while stirring at 140 rpm for a further 45 h. 7800 kg of deionized water were added to 38 kg of this suspension. The suspension was stirred at 70 rpm, and 100 kg of a 10% by weight aqueous $HNO_3$ solution were added. The boron-containing zeolite material having a BEA skeleton structure was separated from this suspension by filtration. The filtercake was washed with deionized water at room temperature until the wash water had a conductivity of less than 150 microsiemens/cm. The filtercake thus obtained was dried in a nitrogen stream.

The zeolitic material thus obtained was subjected to a spray drying operation in a spray tower with the following spray drying conditions:
Drying gas, nozzle gas: technical grade nitrogen
Drying gas temperature:
 spray tower temperature (inside): 235° C.
 spray tower temperature (outside): 140° C.
Nozzle:
 Top component nozzle supplied by Gerig; size 0
 Nozzle gas temperature: room temperature
 Nozzle gas pressure: 1 bar
Mode of operation: nitrogen direct
Apparatus used: spray tower with a nozzle
Configuration: spray tower-filter-scrubber
Gas flow rate: 1500 kg/h
Filter material: Nomex® needle-felt 20 m$^2$
Metering via flexible peristaltic pump: SP VF 15 (supplier: Verder)

The spray tower comprised a vertical cylinder having a length of 2650 mm and a diameter of 1200 mm, with conical narrowing of the cylinder at the base. The length of the cone was 600 mm. At the top of the cylinder were disposed the atomization devices (a two-phase nozzle). The spray-dried material was separated from the drying gas in a filter downstream of the spray tower, and the drying gas was conducted through a scrubber. The suspension was conducted through the inner orifice of the nozzle, and the nozzle gas was conducted through the annular slot that surrounded the orifice.

The spray-dried material was then calcined at 500° C. for 5 h. The calcined material had a molar $B_2O_3:SiO_2$ ratio of 0.045, a total organic carbon (TOC) content of 0.08% by weight, a crystallinity determined by XRD of 100%, and a specific BET surface area determined to DIN 66131 of 498 m$^2$/g.

II.2.2 Deboronation—Formation of Vacant Tetrahedral Sites 840 kg of deionized water were provided in a vessel provided with a reflux condenser. While stirring at 40 rpm, 28 kg of the spray-dried and calcined zeolitic material were added as described above in II.2.1. Subsequently, the vessel was closed and the reflux condenser was put into operation. The stirring rate was increased to 70 rpm. While stirring at 70 rpm, the contents of the vessel were heated to 100° C. within one hour and kept at this temperature for 20 h. Then the contents of the vessel were cooled to a temperature below 50° C.

The resulting deboronated zeolitic material having a BEA skeleton structure was separated from the suspension by filtration under a nitrogen pressure of 2.5 bar and washed with deionized water four times at room temperature. After filtration, the filtercake was dried in a nitrogen stream for 6 h.

The resulting deboronated zeolitic material, after resuspension in deionized water, was spray-dried under the conditions mentioned above in II.2.1. The solid content of aqueous suspension was 15% by weight, based on the total weight of the suspension. The zeolitic material obtained had a molar $B_2O_3:SiO_2$ ratio of less than 0.002, a crystallinity determined by XRD of 77%, and a specific BET surface area determined to DIN 66131 of 489 m$^2$/g.

II.2.3 Synthesis of an Sn Beta-Zeolite 200 g of the deboronated zeolitic material having a BEA skeleton structure according to II.2.2 were combined in a mill (mill type: Microton MB550) with 56.8 g of tin(II) acetate (Sn(OAc)$_2$ [CAS no.: 638-39-1]), and the mixture was ground at 14 000 rpm (revolutions per minute) for 15 minutes. After the grinding, the mixture was transferred to a porcelain basket and calcined under air at 500° C. at a heating rate of 2 K/min for 3 h.

The powder material obtained had an Sn content of 14.4% by weight, a silicon (Si) content of 38% by weight and a TOC of less than 0.1% by weight.

II.2.4 Production of a Tin-Containing Material Having BEA Skeleton Structure with Acid Treatment 200 g of zeolitic material obtained according to II.2.3 were provided in a round-bottom flask, and 6000 g of 30% by weight aqueous HNO$_3$ solution having a pH in the range from 0 to 1 were added. The mixture was stirred at a temperature of 100° C. for a time span of 20 h (200 rpm). The suspension was filtered and the filtercake was then washed with deionized water at room temperature until the wash water had a pH of about 7.

The zeolitic material obtained was dried at 120° C. for 10 h and calcined by means of heating to 550° C. (2 K/min) and then heating at 550° C. for 10 h. The dried and calcined zeolitic material had an Si content of 36% by weight and an Sn content of 14.0% by weight. In addition, the zeolitic material had a specific BET surface area determined to DIN 66131 of 402 m$^2$/g.

II.2.5 Preparation of a P-Treated Sn-Containing Material Having a BEA Skeleton Structure 191 g of the zeolitic material obtained according to II.2.4 were mixed with 23.88 g of ammonium dihydrogenphosphate (NH$_4$H$_2$PO$_4$). 149.6 g of deionized water were added and mixed carefully. The suspension was dried in a vacuum oven at 110° C. for 12 h. The dried material was calcined in an oven heated to 500° C. with a temperature ramp of 2 K/min under air for 5 h. Subsequently, the dried and calcined material was cooled to room temperature. 214 g of Sn-containing material having a BEA skeleton structure were obtained.

The Sn-containing zeolitic material having BEA skeleton structure had the following composition: 12.7% by weight of Sn, 32% by weight of Si, <0.1% by weight of C (TOC), 2.8% by weight of P. The BET surface area was determined to be 267 m$^2$/g in accordance with DIN 66131.

II.2.6 Forming of the P-Treated Sn-Containing Material with BEA Skeleton Structure A kneader was charged with 200 g of the zeolitic material obtained according to II.2.5 and mixed with an acidic solution prepared from 6 g of HNO$_3$ (65% by weight) dissolved in 20 mL of distilled water. The suspension was mixed (kneaded) for 10 min. Added to the resulting mixture were 10 g of Walocel™ and 26.3 g of Ludox® AS-40, and the mixture was mixed for a further 30 min. Finally, 120 mL of distilled water were added to the mixture and mixed for a further 20 min. The paste was then extruded in a Loomis extruder. Extrudates of 2.0 mm were obtained in a static oven and dried at 120° C. for 5 h, followed by calcination at 500° C. for 5 h under air at a heating rate of 2 K/min. The resulting extrudates were divided into a fraction of 1.0-1.6 mm.

The calcined extrudates had a bulk density of 490 g/L with a mechanical strength of 3 N. The elemental composition was Sn 12.7% by weight, Si 34% by weight and TOC<0.1% by weight and P 2.8% by weight.

II.3 Catalyst 3
Oxidic Catalyst Comprising Vanadium, Tungsten, Phosphorus and Bismuth on Silica Support 67 g of bismuth acetate were added to an aqueous citric acid solution (100 g of acid in 1 liter of deionized water). The mixture was heated to 80° C. and stirred for 30 minutes. 117.5 g of phosphoric acid (85%), 116 g of a colloidal silica suspension (Ludox AS 40) and 100 g of ethylene glycol were added successively. The mixture was stirred at 80° C. for a further 30 minutes. 110 g of ammonium metavanadate and 169 g of ammonium metatungstate were added successively. 20 g of acetyl cellulose were slurried with deionized water and added to the mixture. The final mixture was stirred at 80° C. for three hours. The mixture was concentrated in a rotary evaporator at 60° C. and 45 mbar. The resulting solid material was dried further in a drying oven at 100° C. for 16 h.

The resulting solid material was calcined in accordance with the following temperature profile:
i) heating from room temperature to 160° C. at a rate of 10° C. per minute;
ii) heating at 160° C. for 2 hours;
iii) heating from 160° C. to 250° C. at a rate of 3° C. per minute;
iv) heating at 250° C. for 2 hours;
v) heating from 250° C. to 300° C. at a rate of 3° C. per minute;
vi) heating at 300° C. for 6 hours;
vii) heating from 300° C. to 450° C. at a rate of 3° C. per minute;
viii) heating at 450° C. for 6 hours.

II.4 Catalyst 4
Oxidic Catalyst Comprising Vanadium, Tungsten, Phosphorus and Bismuth on Silica Support 167.5 g of ammonium metavanadate were added to 3 liters of a 20% by weight aqueous solution of citric acid. The mixture was heated to 50° C. and stirred until dissolution was complete. 116 g of a colloidal silica suspension (Ludox AS 40) were added, followed by 227.8 g of ethylene glycol. The mixture was heated to 80° C. and stirred for 30 minutes. 35.3 g of ammonium metatungstate were dissolved in 500 mL of deionized water and added dropwise to the mixture. The mixture was then stirred at 80° C. for 15 minutes. 347.2 g of bismuth nitrate hexahydrate were dissolved in 480 mL of a 10% nitric acid solution. The acidic bismuth solution was added dropwise to the previous mixture and stirred at 80° C. for 30 minutes, then cooled down to 30° C. while stirring constantly. 1232 mL of a 2% solution of methyl cellulose were added and then the mixture was stirred for a further 30 minutes. Finally, 303.7 g of an 85% phosphoric acid solution were added and the mixture was stirred for 30 minutes. The resulting mixture was dried at 80° C. in a drying oven for 48 h.

For safety reasons, the resulting solid material was calcined in an atmosphere having 3% by volume of $O_2$/97% by volume of $N_2$ in accordance with the following temperature profile:
i) heating from room temperature to 160° C. at a rate of 10° C. per minute;
ii) heating at 160° C. for 2 hours;
iii) heating from 160° C. to 250° C. at a rate of 3° C. per minute;
iv) heating at 250° C. for 2 hours;
v) heating from 250° C. to 300° C. at a rate of 3° C. per minute;
vi) heating at 300° C. for 6 hours;
vii) heating from 300° C. to 450° C. at a rate of 3° C. per minute;
viii) heating at 450° C. for 6 hours.

III. Setup and Operation of the Pilot Plant
III.1 Example 1: Determination of the Maximum Amount of Acrylic Acid in Stream S1

The apparatus consisted of a fixed bed reactor (bed length about 90 cm, diameter 16 mm, 1.4541 stainless steel) heated in four zones and having 3 sampling points for online GC measurements (inlet, middle, outlet) and two reactant metering zones. In order to charge the plant with formaldehyde and acetic acid, the reservoir vessel was initially charged with acetic acid or acetic acid solution and formaldehyde or formalin solution.

Formalin (49% by weight of formaldehyde in water) was conveyed by means of a Fink HPLC pump and evaporated completely by means of a microevaporator (passage length 60 mm, passage width 0.2 mm, alloy 22, 2.4602) (wall temperature about 280° C.). In order to prevent paraformaldehyde from precipitating out in the cold conduit, the reservoir vessel and the distance up to the evaporator were heated to 60° C. By means of a three-way tap, it was possible to run formalin either in a circuit back into the vessel or else in the evaporator direction.

A Fink HPLC pump was used to pump acetic acid into a helical tube evaporator (diameter 8 mm, length about 2 m, 1.4571 stainless steel), which completely evaporated therein (wall temperature about 200° C.) and mixed with a stream comprising nitrogen.

The stream comprising the evaporated formalin and the stream comprising the evaporated acetic acid and nitrogen were combined and passed as stream S1 via a pipeline heated to 150-200° C. through a static mixer (diameter 10 mm, length 80 mm, 1.4541 stainless steel) containing wire mesh into the reactor heated to 320° C. (outer wall) (WHSV: 1.4 kg/kg/h). After passing through an unfilled region (length 2.8 cm), the gas stream arrived at a first steatite bed (mass 33 g, bed height 16 cm, 4-5 mm balls). The downstream catalyst bed was divided into two (mass of each 40 g, bed height 23 cm) and was interspersed with a second steatite bed (mass 42 g, bed height 20 cm, 4-5 mm balls). The overall bed rested on a catalyst support of about 3 cm in height, with a third steatite bed (mass 14 g, bed height 7 cm, 4-5 mm balls) concluding the reactor outlet. Within the reactor was a thermowell of thickness 3.17 mm, which was used to measure a temperature profile along the reactor. The reaction was conducted at a pressure of 1100 mbar (absolute).

The reactor offgas was passed to a total combustion unit downstream of the reactor outlet. For protection against blockages by catalyst dusts, a filter station was installed downstream of the reactor outlet. In the total combustion unit, all components were incinerated with air metered in additionally (about 2000 L (STP)/h) and nitrogen which can be metered in additionally (about 1000 L (STP)/h) to give water and carbon dioxide. Constant pressure conditions in the reactor over different test runs were established by partly throttling the valves in the filter station. The total combustion unit air was heated to 300-400° C. by means of heating sleeves. The combustion temperature in the combustion catalyst bed varied with the organic carbon loading of the reactor offgases and was between 250° C. and 500° C. The offgas from the total combustion unit was passed through a separator (T=5-15° C.). The offgas that remains thereafter was passed into the offgas conduit.

Acrylic acid (ACR) was added to the acetic acid-comprising stream in different contents (ACR content, ACR input). Various catalysts were used. The individual streams were analyzed by gas chromatography. The results, and details of ACR contents, are shown in tables 1 to 4 below, and presented in graph form in FIGS. 2 and 3. Since stream S1 was entirely gaseous, rather than the molar figures for the ratio of acrylic acid to the sum total of formaldehyde+acetic acid, the figures are given in % by volume.

TABLE 1

Catalyst 1

| Experiment | Ratio of acrylic acid to sum total of formaldehyde + acetic acid at reactor inlet [vol/vol] | Yield of acrylic acid based on formaldehyde conversion Mean [%] | Yield of acrylic acid based on acetic acid conversion Mean [%] | Formaldehyde conversion Mean [%] | Acetic acid conversion Mean [%] | Selectivity for acrylic acid based on formaldehyde conversion Mean [%] | Selectivity for acrylic acid based on acetic acid conversion Mean [%] |
|---|---|---|---|---|---|---|---|
| Cat1-A | 0.014 | 30.77 | 36.78 | 46.96 | 48.45 | 65.52 | 75.91 |
| Cat1-B | 0.036 | 30.37 | 33.19 | 46.62 | 45.03 | 65.14 | 73.71 |
| Cat1-C | 0.063 | 29.95 | 32.53 | 44.53 | 44.61 | 67.26 | 72.92 |
| Cat1-D | 0.090 | 23.95 | 26.53 | 44.12 | 41.24 | 54.28 | 64.33 |

TABLE 2

Catalyst 2

| Experiment | Ratio of acrylic acid to sum total of formaldehyde + acetic acid at reactor inlet [vol/vol] | Yield of acrylic acid based on formaldehyde conversion Mean [%] | Yield of acrylic acid based on acetic acid conversion Mean [%] | Formaldehyde conversion Mean [%] | Acetic acid conversion Mean [%] | Selectivity for acrylic acid based on formaldehyde conversion Mean [%] | Selectivity for acrylic acid based on acetic acid conversion Mean [%] |
|---|---|---|---|---|---|---|---|
| Cat2-A | 0.032 | 2.7 | 3.07 | 2.5 | 9.9 |  | 32.43 |
| Cat2-B | 0.072 | 1.98 | 1.83 | 6.14 | 10.38 | 36.30 | 18.00 |
| Cat2-C | 0.098 | 1.35 | 1.45 | 1.38 | 7.58 | 34.20 | 24.20 |
| Cat2-D | 0.018 | 3.628 | 3.158 | 8.38 | 11.08 | 40.26 | 32.15 |

TABLE 3

Catalyst 3

| Experiment | Ratio of acrylic acid to sum total of formaldehyde + acetic acid at reactor inlet [vol/vol] | Yield of acrylic acid based on formaldehyde conversion Mean [%] | Yield of acrylic acid based on acetic acid conversion Mean [%] | Formaldehyde conversion Mean [%] | Acetic acid conversion Mean [%] | Selectivity for acrylic acid based on formaldehyde conversion Mean [%] | Selectivity for acrylic acid based on acetic acid conversion Mean [%] |
|---|---|---|---|---|---|---|---|
| Cat3-A | 0.025 | 18.43 | 17.46 | 32.26 | 30.9 | 60.36 | 56.81 |
| Cat3-B | 0.048 | 14.6 | 20.51 | 21.76 | 29.33 | 77.61 | 75.20 |
| Cat3-C | 0.068 | 14.4 | 20.02 | 28.68 | 31.71 | 55.63 | 66.33 |
| Cat3-D | 0.090 | 12.32 | 17.83 | 38.98 | 31.13 | 37.04 | 61.43 |
| Cat3-E | 0.027 | 14.53 | 19.14 | 23.03 | 31.47 | 56.34 | 62.03 |

TABLE 4

Catalyst 4

| Experiment | Ratio of acrylic acid to sum total of formaldehyde + acetic acid at reactor inlet [vol/vol] | Yield of acrylic acid based on formaldehyde conversion Mean [%] | Yield of acrylic acid based on acetic acid conversion Mean [%] | Formaldehyde conversion Mean [%] | Acetic acid conversion Mean [%] | Selectivity for acrylic acid based on formaldehyde conversion Mean [%] | Selectivity for acrylic acid based on acetic acid conversion Mean [%] |
|---|---|---|---|---|---|---|---|
| Cat4-A | 0.030 | 27.83 | 27.21 | 42.63 | 40.28 | 65.34 | 67.55 |
| Cat4-B | 0.053 | 29.12 | 30.11 | 38.11 | 38.93 | 77.53 | 77.26 |
| Cat4-C | 0.076 | 26.80 | 32.73 | 32.59 | 37.31 | 82.55 | 82.34 |
| Cat4-D | 0.038 | 24.54 | 29.79 | 34.35 | 39.60 | 71.85 | 75.72 |
| Cat4-E | 0.102 | 12.91 | 14.93 | 45.56 | 51.47 | 30.21 | 32.42 |

Figure 2:
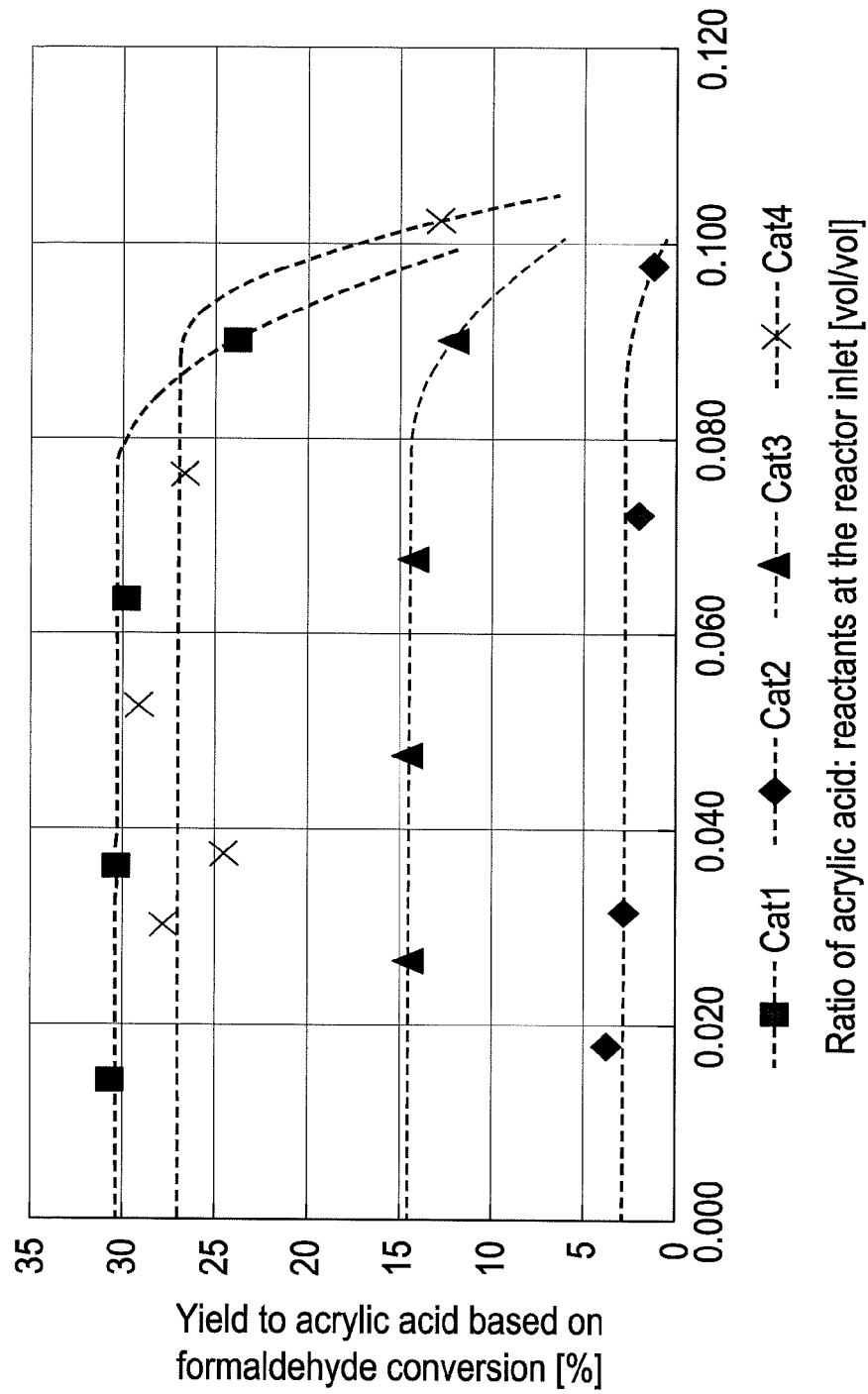
FIG. 2 shows a plot of the acrylic acid yield based on the formaldehyde conversion in % (ordinate, from 0% to 35%) versus the molar ratio of acrylic acid to the sum total of formaldehyde and acetic acid (reactants) in stream S1 (abscissa, from 0 to 0.12 vol/vol) for experiment 1 with the results from tables 1-4.
Figure 3:
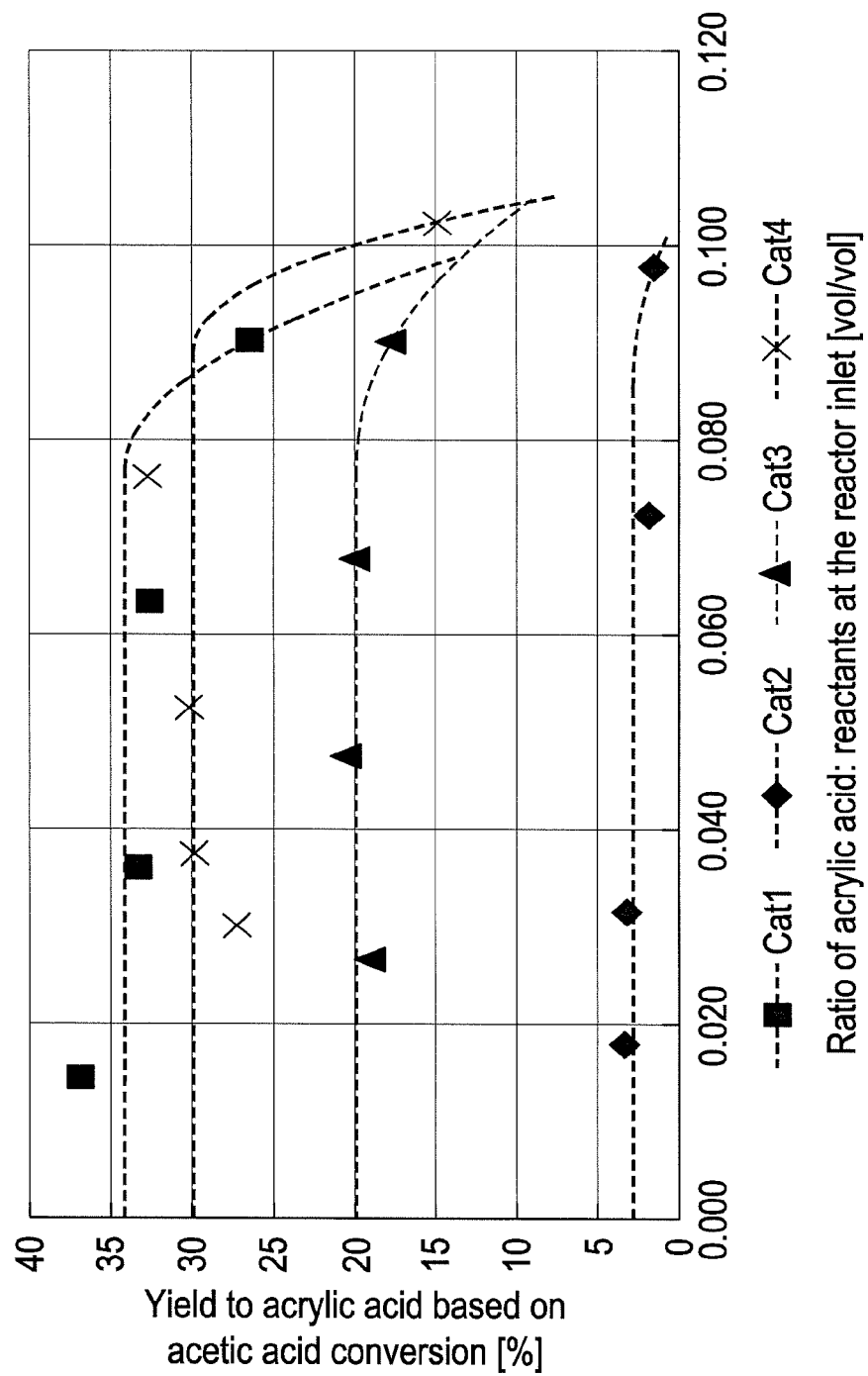
FIG. 3 shows a plot of the acrylic acid yield based on the acetic acid conversion in % (ordinate) versus the molar ratio of acrylic acid to the sum total of formaldehyde and acetic acid (reactants) in stream S1 (abscissa, from 0 to 0.12 vol/vol) for experiment 1 with the results from tables 1-4.

As can be seen from the above tables 1-4 and especially shown by FIGS. 2 and 3, the presence of acrylic acid in stream S1 was acceptable for the acrylic acid production in a molar ratio relative to the sum total of the reactants, formaldehyde and acetic acid, up to a value of 0.3:1. It was apparent that preferred molar ratios of acrylic acid to the sum total of the reactants, formaldehyde and acetic acid, in stream S1, were in the range of up to 0.1:1, more preferably of up to 0.09:1, further preferably of up to 0.08:1, further preferably of up to 0.07:1.

III.2 Example 2: Determination of the Minimum Acrylic Acid Content in Stream S1

The example which follows was run with the aid of the process simulation program CHEMASIM from BASF. The essential compositions and properties of the streams shown in FIG. 1 can be found in tables 5 and 6. Mass balances are completed by any offgas streams not mentioned/shown.

The acetic acid and formalin solution reactants (~49% by weight of formaldehyde, ~49% by weight of water, ~2% by weight of methanol) were subjected to total evaporation (i) in a suitable heat transferer, diluted with inert gas (nitrogen), and fed as stream S1, optionally after mixing with the recycled streams S2b_rec and/or S3 and/or S5 and/or S8, in gaseous form to the reaction zone (ii), charged with the aldol condensation reactor.

In the reaction zone (ii), stream S1 was contacted at 370° C. and 1.1 bar absolute with a catalyst of the empirical formula $VO(PO)_4$ shaped into cylindrical extrudates having a cross-sectional area diameter of 3 mm and an average length of 20 mm. This was done using a shell and tube reactor, with the catalytically active fixed bed within the catalyst tubes, around which fluid heat carrier flowed.

The gaseous reactor output S2 was cooled down to about 40° C. in a suitable heat transferer in (iii), and partly condensed at the same time. The uncondensed portion S2b which comprised predominantly low-boiling components and inert gases, after removing at least a portion of S2b, S2b_Purge, was recycled upstream of the reactor in (ii) as S2b_Rec.

The condensed portion of S2, S2a, was guided into a distillation column in (iv.1). This column was designed as a tray column equipped with a number of crossflow trays equivalent to about 30 theoretical plates, and was operated in rectificative mode. The feed stream was at about the 10th theoretical plate. A return stream consisting of at least a portion of S3 (not shown in FIG. 1) was applied to the uppermost tray. The vapor from the evaporator (not shown in FIG. 1) which was executed as a shell and tube circulation evaporator and was operated with 4 bar steam as heat carrier was conducted into the column below the first tray. The column in (iv.1) was operated at a top pressure of 1.3 bar absolute; the bottom temperature was about 140° C., and the top temperature about 105° C. The vapors from the column were at least partly condensed in a shell and tube apparatus (not shown in FIG. 1), with conduction of the liquid component into a distillate collection vessel and division thereof into return stream and distillate draw stream S3 therein. At the bottom of the column in (iv.1), a liquid bottom stream S4 was withdrawn.

Stream S4 was passed into a distillation column in (iv.2). This column was designed as a tray column equipped with a number of dual-flow trays equivalent to about 20 theoretical plates, and was operated in rectificative mode. The feed stream was at about the 8th theoretical plate. A return stream consisting of at least a portion of S5 (not shown in FIG. 1) was applied to the uppermost tray. The vapor from the evaporator (not shown in FIG. 1) which was executed as a shell and tube circulation evaporator and was operated with 4 bar steam as heat carrier was conducted into the column below the first tray. The column in (iv.2) was operated at a top pressure of 100 mbar absolute; the bottom temperature was about 105° C., and the top temperature about 40° C. The vapors from the column were at least partly condensed in a shell and tube apparatus (not shown in FIG. 1), with conduction of the liquid component into a distillate collection vessel and division thereof into return stream and distillate draw stream S5 therein. Stream S5 was recycled upstream of the reactor in (ii). Acrylic acid was drawn off in liquid form as S6 in the bottom of the column in (iv.2).

Stream S3 was passed into a distillation column in (iv.3). This column was designed as a column with random packing, equipped with a random packing bed height equivalent to about 20 theoretical plates, and was operated in rectificative mode. The feed stream was at about the 5th theoretical plate. A return stream consisting of at least a portion of S7 (not shown in FIG. 1) was applied to the uppermost tray. The vapor from the evaporator (not shown in FIG. 1) which was executed as a shell and tube circulation evaporator and was operated with 4 bar steam as heat carrier was conducted into the column below the first tray. The column in (iv.3) was operated at a top pressure of 90 mbar absolute; the bottom temperature was about 60° C., and the top temperature about 40° C. The vapors from the column were at least partly condensed in a shell and tube apparatus (not shown in FIG. 1), with conduction of the liquid component into a distillate collection vessel and division thereof into return stream and distillate draw stream S7 therein. Stream S7 was disposed of as wastewater in need of treatment. At the bottom of the column in (iv.3), a liquid bottom stream S8 was withdrawn and recycled completely upstream of the reactor in (ii).

Figure 4:
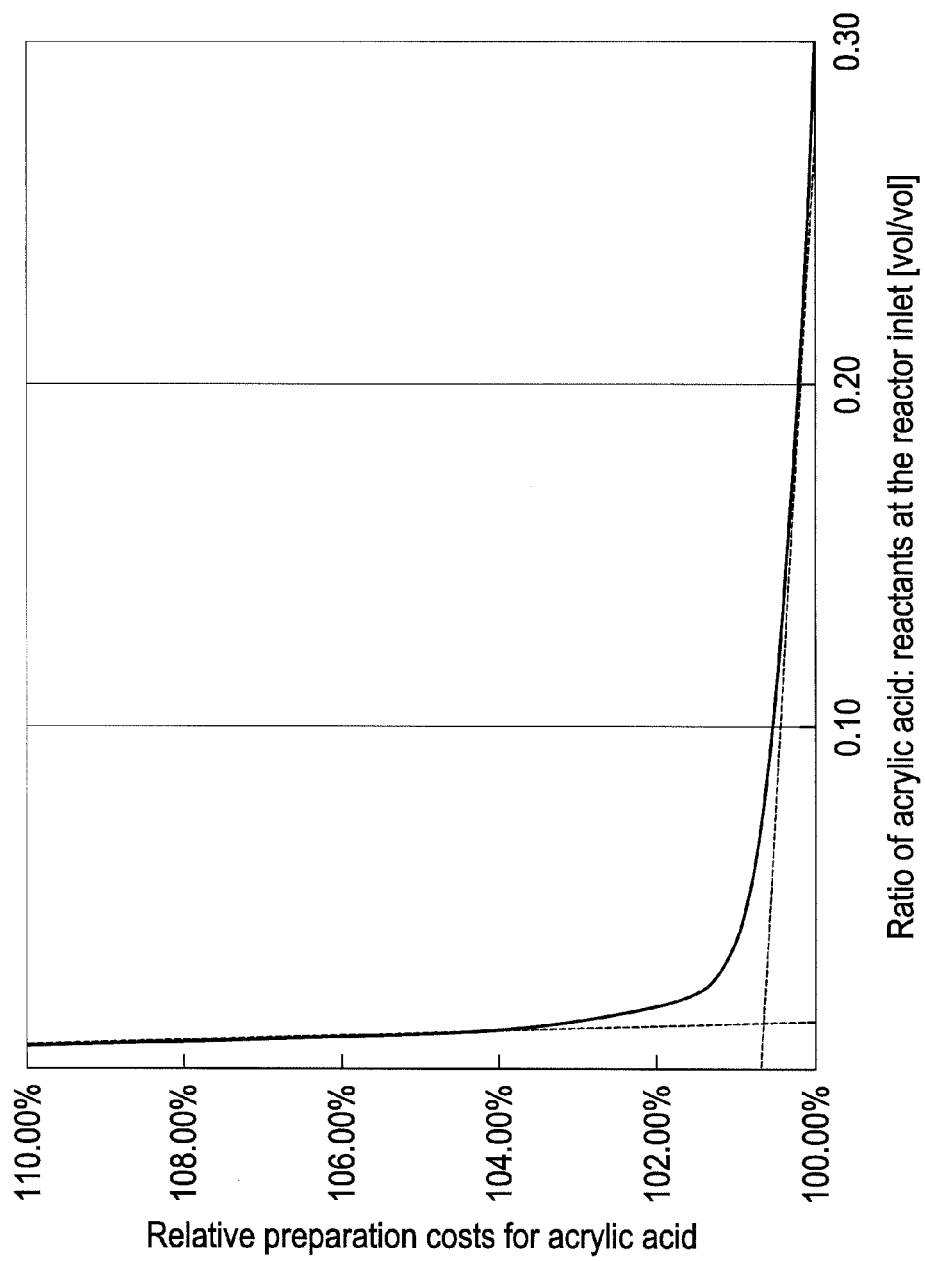
FIG. 4 shows a plot of the relative preparation costs for acrylic acid (ordinate, from 100% to 110%) versus the molar ratio of acrylic acid to the sum total of formaldehyde and acetic acid in stream S1 (abscissa, 0 to 0.3 vol/vol).

With reference to the overall simulation of the process described in example 2, the influence of the amount of acrylic acid recycled on the economic viability of the process was illustrated. With the aid of the CHEMASIM process simulator and an in-house BASF SE tool for realistic assessment of capital and operating costs of chemical processes, the preparation costs for acrylic acid by the process described in example 2 were examined as a function of the amount of acrylic acid permitted in the recycle streams. The relative value estimated for the acrylic acid preparation costs (based on the costs at a molar ratio of acrylic acid to the sum total of formaldehyde and acetic acid of 0.3:1 in the reactor inlet) as a function of the molar ratio of acrylic acid to the sum total of formaldehyde and acetic acid in the reactor inlet (S1) is shown in FIG. 4. The rise in the preparation costs with a smaller permitted ratio of acrylic acid to the sum total of the reactants at the reactor inlet was attributable to a crucial degree to the rising energy costs which are caused by the higher distillative separation intensity and hence rising demand for steam and cooling water in the column (iv.2).

It is apparent from the thermodynamic simulation that the lower limit in the molar ratio of acrylic acid to reactants (formaldehyde+acetic acid) in stream S1 was 0.005:1; the preferred lower limit was seen to be a molar ratio of acrylic acid to reactant in stream S1 of 0.02:1. Since stream S1 was entirely gaseous, rather than the molar figures for the ratio of acrylic acid to the sum total of formaldehyde+acetic acid, the figures were given in % by volume.

TABLE 5

Stream bar (1/2)

|  | Abbreviation | M [kg/kmol] | Stream S1 [kg/h] | Stream S1 [% by wt.] | Stream S2 [kg/h] | Stream S2 [% by wt.] | Stream S2a [kg/h] | Stream S2a [% by wt.] |
|---|---|---|---|---|---|---|---|---|
| Formaldehyde | FA | 30.03 | 20769 | 8.73 | 8307.7 | 3.49 | 8033.4 | 9.35 |
| Acetic acid | ACE | 60.05 | 41540 | 17.46 | 16616 | 6.98 | 15672 | 18.24 |
| Acrylic acid | ACR | 72.07 | 5538.7 | 2.33 | 32680 | 13.73 | 31475 | 36.63 |
| Water | H2O | 18.02 | 24332 | 10.23 | 33565 | 14.11 | 30023 | 34.94 |
| Methanol | MEOH | 32.04 | 552.1 | 0.23 | 220.8 | 0.09 | 180.5 | 0.21 |
| Formic acid | FAC | 46.03 | 564.0 | 0.24 | 564.0 | 0.24 | 531.9 | 0.62 |
| Propionic acid | PRA | 74.08 | 10.9 | 0.00 | 10.9 | 0.00 | 10.7 | 0.01 |
| Carbon dioxide | CO2 | 44.01 | 22160 | 9.31 | 27685 | 11.64 |  |  |
| Oxygen | O2 | 32.00 | 6763.4 | 2.84 | 2580.6 | 1.08 |  |  |
| Carbon monoxide | CO | 28.01 |  |  |  |  |  |  |
| Hydrogen | H2 | 2.02 |  |  |  |  |  |  |
| Nitrogen | N2 | 28.01 | 115703 | 48.63 | 115703 | 48.63 |  |  |
| Sum total |  |  | 237933 | 100.0 | 237933 | 100.0 | 85927 | 100.0 |
| Volumetric flow rate | V | m³/h | 293553 |  | 375736 |  | 82.64 |  |
| Density | ρ | kg/m³ | 0.811 |  | 0.633 |  | 1039.7 |  |
| Viscosity eta | η | mPa s | 0.027 |  | 0.027 |  | 0.997 |  |
| Specific heat | c_p | kJ/kg/K | 1.387 |  | 1.398 |  | 2.901 |  |
| Surface tension | σ | N/m |  |  |  |  | 0.039 |  |
| Mean molar mass | M | kg/kmol | 31.0 |  | 30.8 |  | 32.4 |  |
| Temperature | T | °C. | 370.0 |  | 370.0 |  | 40.0 |  |
| Boiling pressure | BP | bar |  |  |  |  |  |  |
| Pressure | p | bar | 1.400 |  | 1.100 |  | 1.400 |  |

|  | Stream S2b [kg/h] | Stream S2b [% by wt.] | Stream S2b_Purge [kg/h] | Stream S2b_Purge [% by wt.] | Stream S2b_Rec [kg/h] | Stream S2b_Rec [% by wt.] | Stream S3 [kg/h] | Stream S3 [% by wt.] |
|---|---|---|---|---|---|---|---|---|
| Formaldehyde | 274.3 | 0.18 | 51.7 | 0.17 | 206.6 | 0.17 | 8030.6 | 19.33 |
| Acetic acid | 943.8 | 0.62 | 188.8 | 0.62 | 755.0 | 0.62 | 3287.0 | 7.91 |
| Acrylic acid | 1205.1 | 0.79 | 241.0 | 0.79 | 964.1 | 0.79 | 472.1 | 1.14 |
| Water | 3541.7 | 2.33 | 707.1 | 2.33 | 2828.5 | 2.33 | 29579 | 71.19 |
| Methanol | 40.4 | 0.03 | 6.8 | 0.02 | 27.2 | 0.02 | 179.9 | 0.43 |
| Formic acid | 32.2 | 0.02 | 6.4 | 0.02 | 25.7 | 0.02 | 0.1 | 0.00 |
| Propionic acid | 0.2 | 0.00 | 0.0 | 0.00 | 0.2 | 0.00 | 0.0 | 0.00 |
| Carbon dioxide | 27685 | 18.21 | 5537.0 | 18.21 | 22148 | 18.21 |  |  |
| Oxygen | 2580.6 | 1.70 | 516.1 | 1.70 | 2064.5 | 1.70 |  |  |
| Carbon monoxide |  |  |  |  |  |  |  |  |
| Hydrogen |  |  |  |  |  |  |  |  |
| Nitrogen | 115703 | 76.12 | 23141 | 76.12 | 92563 | 76.12 |  |  |
| Sum total | 152007 | 100.0 | 30401 | 100.0 | 121605 | 100.0 | 41549 | 100.0 |
| Volumetric flow rate | 94258 |  | 18852 |  | 75406 |  | 41.41 |  |
| Density | 1.613 |  | 1.613 |  | 1.613 |  | 1003.3 |  |
| Viscosity eta | 0.018 |  | 0.018 |  | 0.018 |  | 0.412 |  |
| Specific heat | 1.095 |  | 1.095 |  | 1.095 |  | 3.636 |  |
| Surface tension |  |  |  |  |  |  | 0.049 |  |
| Mean molar mass | 29.9 |  | 29.9 |  | 29.9 |  | 21.0 |  |
| Temperature | 40.0 |  | 40.0 |  | 40.0 |  | 105.7 |  |
| Boiling pressure |  |  |  |  |  |  | 1.300 |  |
| Pressure | 1.400 |  | 1.400 |  | 1.400 |  | 1.300 |  |

TABLE 6

Stream bar (2/2)

|  | Abbreviation | M [kg/kmol] | Stream 54 [kg/h] | Stream 54 [% by wt.] | Stream S5 [kg/h] | Stream S5 [% by wt.] | Stream S6 [kg/h] | Stream S6 [% by wt.] | Stream S7 [kg/h] | Stream S7 [% by wt.] | Stream S8 [kg/h] | Stream S8 [% by wt.] |
|---|---|---|---|---|---|---|---|---|---|---|---|---|
| Formaldehyde | FA | 30.03 | 2.8 | 0.01 | 2.8 | 0.02 |  |  | 109.7 | 0.50 | 7920.9 | 40.40 |
| Acetic acid | ACE | 60.05 | 12385 | 27.91 | 12331 | 70.82 | 54 | 0.20 | 0.0 | 0.00 | 3287.0 | 16.77 |
| Acrylic acid | ACR | 72.07 | 31003 | 69.86 | 4102.4 | 23.56 | 26901 | 99.76 | 0.0 | 0.00 | 4721 | 2.41 |
| Water | H2O | 18.02 | 443.8 | 1.00 | 443.8 | 2.55 | 0.0 | 0.00 | 21657 | 98.70 | 7920.9 | 40.40 |

TABLE 6-continued

Stream bar (2/2)

| | Abbreviation | M [kg/kmol] | Stream S4 [kg/h] | Stream S4 [% by wt.] | Stream S5 [kg/h] | Stream S5 [% by wt.] | Stream S6 [kg/h] | Stream S6 [% by wt.] | Stream S7 [kg/h] | Stream S7 [% by wt.] | Stream S8 [kg/h] | Stream S8 [% by wt.] |
|---|---|---|---|---|---|---|---|---|---|---|---|---|
| Methanol | MEOH | 32.04 | 0.6 | 0.00 | 0.6 | 0.00 | | | 175.9 | 0.80 | 3.9 | 0.02 |
| Formic acid | FAC | 46.03 | 531.7 | 1.20 | 531.7 | 3.05 | 0.0 | 0.00 | | | 0.1 | 0.00 |
| Propionic acid | PRA | 74.08 | 10.7 | 0.02 | 0.5 | 0.00 | 10 | 0.01 | | | 0.0 | 0.00 |
| Carbon dioxide | $CO_2$ | 44.01 | | | | | | | | | | |
| Oxygen | $O_2$ | 32.00 | | | | | | | | | | |
| Carbon monoxide | CO | 28.01 | | | | | | | | | | |
| Hydrogen | $H_2$ | 2.02 | | | | | | | | | | |
| Nitrogen | $N_2$ | 28.01 | | | | | | | | | | |
| Sum total | | | 44378 | 100.0 | 17413 | 100.0 | 26965 | 100.0 | 21943 | 100.0 | 19605 | 100.0 |
| Volumetric flow rate | V | $m^3/h$ | 48.80 | | 16.92 | | 28.40 | | 22.23 | | 17.81 | |
| Density | $\rho$ | $kg/m^3$ | 909.3 | | 1028.9 | | 949.6 | | 987.1 | | 1101.0 | |
| Viscosity eta | $\eta$ | mPa s | 0.293 | | 0.880 | | 0.377 | | 0.665 | | 1.284 | |
| Specific heat | $c\_p$ | kJ/kg/K | 2.900 | | 2.449 | | 2.348 | | 4.166 | | 2.929 | |
| Surface tension | $\sigma$ | N/m | 0.016 | | 0.027 | | 0.019 | | 0.069 | | 0.044 | |
| Mean molar mass | M | kg/kmol | 66.0 | | 58.3 | | 72.0 | | 18.1 | | 25.6 | |
| Temperature | T | °C. | 139.6 | | 40.0 | | 106.4 | | 40.0 | | 62.0 | |
| Boiling pressure | BP | bar | 1.490 | | | | 0.310 | | | | | |
| Pressure | p | bar | 1.490 | | 0.100 | | 0.310 | | 0.090 | | 0.185 | |

The invention claimed is:

1. A process for preparing acrylic acid from formaldehyde and acetic acid, comprising
   (i) providing a gaseous stream S1 comprising formaldehyde, acetic acid and acrylic acid, where a molar ratio of acrylic acid to a sum total of formaldehyde and acetic acid in stream S1 is in a range from 0.005:1 to 0.3:1;
   (ii) contacting stream S1 with an aldol condensation catalyst in a reaction zone to obtain a gaseous stream S2 comprising acrylic acid.

2. The process according to claim 1, wherein the molar ratio of acrylic acid to the sum total of formaldehyde and acetic acid in stream S1 in (i) is in the range from 0.02:1 to 0.1:1.

3. The process according to claim 1, wherein a molar ratio of acetic acid:formaldehyde in stream S1 in (i) is in a range from 0.25:1 to 4.4:1.

4. The process according to claim 1, wherein at least 65% by volume of stream S1 in (i) consists of formaldehyde, acetic acid, acrylic acid, water and inert gas.

5. The process according to claim 1, further comprising
   (iii) partly condensing stream S2 obtained in (ii) by cooling it down to a temperature in the range from 0 to 200° C., with separation of stream S2 into a condensed stream S2a and an uncondensed stream S2b, with optional intermediate storage of stream S2a in a buffer vessel.

6. The process according to claim 5, wherein stream S2b is at least partly recycled into the reaction zone in (ii).

7. The process according to claim 5, wherein the acrylic acid content of stream S2b is in a range from 0.01% to 0.5% by volume, based on a total volume of stream S2b.

8. The process according to claim 5, further comprising
   (iv) working up stream S2a to obtain a product stream SP comprising acrylic acid and a recycling stream SR comprising acrylic acid, where the recycling stream SR comprises not more than 10% of the acrylic acid present in stream S2.

9. The process according to claim 8, wherein at least a portion of the recycling stream SR is recycled into the reaction zone in (ii).

10. The process according to claim 1, wherein stream S1 comprises a stream comprising formaldehyde and acetic acid, of the recycling stream SR and optionally of stream S2b.

11. The process according to claim 8, wherein the workup in (iv) comprises
    (iv.1) removing a portion of the acrylic acid present in stream S2a from stream S2a to obtain a stream S3 depleted of acrylic acid relative to stream S2a, and a stream S4 enriched in acrylic acid relative to stream S2a, comprising acrylic acid and acetic acid;
    (iv.2) removing a portion of the acrylic acid present in stream S4 from stream S4 to obtain a stream S5 depleted of acrylic acid relative to stream S4, comprising acrylic acid and acetic acid, and a stream S6 enriched in acrylic acid relative to stream S4, comprising acrylic acid.

12. The process according to claim 11, wherein the acrylic acid content of stream S3 is in a range from 0.01% to 5% by weight, based on a total weight of stream S3.

13. The process according to claim 11, wherein the acrylic acid content of stream S5 is in a range from 0.1% to 30% by weight, based on a total weight of stream S5.

14. The process according to claim 11, wherein stream S5, at least in part, is at least part of the recycling stream SR which is recycled into the reaction zone in (ii).

15. The process according to claim 11, wherein stream S3, at least in part, is at least part of the recycling stream SR which is recycled into the reaction zone in (ii).

* * * * *